United States Patent
Wilson et al.

(10) Patent No.: US 12,153,057 B2
(45) Date of Patent: Nov. 26, 2024

(54) ANTIBIOTIC THERAPY GUIDANCE BASED ON PROCALCITONIN IN PATIENTS WITH COMORBIDITIES

(71) Applicant: B.R.A.H.M.S GMBH, Hennigsdorf (DE)

(72) Inventors: Darius Wilson, Loerrach (DE); Stefan Kirsch, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 424 days.

(21) Appl. No.: 16/956,330

(22) PCT Filed: Dec. 20, 2018

(86) PCT No.: PCT/EP2018/086130
§ 371 (c)(1),
(2) Date: Jun. 19, 2020

(87) PCT Pub. No.: WO2019/122088
PCT Pub. Date: Jun. 27, 2019

(65) Prior Publication Data
US 2020/0319212 A1    Oct. 8, 2020

(30) Foreign Application Priority Data
Dec. 20, 2017 (EP) ..................... 17209069

(51) Int. Cl.
*G01N 33/74* (2006.01)
*A61K 45/06* (2006.01)
*G01N 33/50* (2006.01)

(52) U.S. Cl.
CPC ........... *G01N 33/74* (2013.01); *G01N 33/502* (2013.01); *A61K 45/06* (2013.01); *G01N 2333/585* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| 8,383,332 B2 | 2/2013 | Bergmann et al. |
| 2010/0143379 A1* | 6/2010 | Bucala ............ A61P 7/06 435/6.15 |
| 2017/0370949 A1 | 12/2017 | Struck et al. |

FOREIGN PATENT DOCUMENTS

| EP | 2320237 A1 | 5/2011 |
| WO | 2011110565 A1 | 9/2011 |

OTHER PUBLICATIONS

International Search Report for PCT/EP2018/086130 dated Jan. 24, 2019.
Christ-Crain, M. et al. "Procalcitonin Guidance of Antibiotic Therapy in Community-acquired Pneumonia: A Randomized Trial," American Journal of Respiratory and Critical Care Medicine, Jan. 1, 2006, pp. 84-93.
Schuetz, P. et al. "Blood biomarkers for personalized treatment and patient management decisions in community-acquired pneumonia," Current Opinion on Infectious Diseases, vol. 26. No. 2, pp. 159-167.

* cited by examiner

*Primary Examiner* — Savitha M Rao
*Assistant Examiner* — Andrew P Lee
(74) *Attorney, Agent, or Firm* — MILLEN, WHITE, ZELANO & BRANIGAN, P.C.; Ryan R. Pool

(57) ABSTRACT

A method for antibiotic therapy guidance, stratification and/or control in a patient with one or more comorbidities comprising an impaired innate immune response and suspected of having an infection. Also, a method for antibiotic therapy guidance, stratification and/or control in a patient with one or more comorbidities comprising an impaired innate immune response, wherein the comorbidity is preferably selected from the group comprising metabolic disorder (obesity), diabetes, hypertension, renal disease, thrombosis, malignancy or cancer, and suspected of having an infection. In particular, the method comprises providing a sample from said patient and determining a level of PCT or fragment(s) thereof in said sample, wherein the level of PCT or fragment(s) thereof in said sample is indicative of whether an initiation or a change of an antibiotic treatment is required. Furthermore, a kit for carrying out the method of the present invention.

15 Claims, No Drawings

ANTIBIOTIC THERAPY GUIDANCE BASED ON PROCALCITONIN IN PATIENTS WITH COMORBIDITIES

The invention relates to a method for antibiotic therapy guidance, stratification and/or control in a patient with one or more comorbidities comprising an impaired innate immune response and suspected of having an infection. The method also relates to a method for antibiotic therapy guidance, stratification and/or control in a patient with one or more comorbidities comprising an impaired innate immune response, wherein the comorbidity is preferably selected from the group comprising metabolic disorder (obesity), diabetes, hypertension, renal disease, thrombosis, malignancy or cancer, and suspected of having an infection. In particular, the method comprises providing a sample from said patient and determining a level of PCT or fragment(s) thereof in said sample, wherein the level of PCT or fragment(s) thereof in said sample is indicative of whether an initiation or a change of an antibiotic treatment is required. Furthermore, the invention also relates to a kit for carrying out the method of the present invention.

BACKGROUND OF THE INVENTION

An early diagnosis and accurate assessment of disease severity in patients with symptoms of an infectious disease is considered critical in improving survival rates and outcomes through targeted therapeutic guidance. This is complicated, however, by the non-specific signs and symptoms of the disease, and exacerbated by an ageing population, a developing resistance to antibiotics, and an enhanced use of immunosuppressives and foreign material in the body[1]. Furthermore, the timely use of antibiotics is of paramount importance, with higher mortality rates shown in response to delayed therapeutic intervention[2,3]. Since the majority of sepsis episodes initially develop in the community, the incidence of which may even be largely underestimated[4]; the earliest opportunity for a targeted clinical intervention is for example at the initial point of hospitalisation—the emergency department (ED).

Patients checking into the emergency department with symptoms of an infection can have one or more comorbidities related to metabolic disorders, respiratory syndromes, cardiovascular diseases or malignancies, amongst others. Some comorbidities can be associated with an altered innate immune response (Falagas M. E. et al. Lancet Infect Dis. 2006 July; 6(7):438-46; Geerlings S. E. et al. FEMS Immunology and Medical Microbiology 26 (1999) 259-265) lacking an adequate response against invading pathogens which creates an increased risk for subsequent complications such as the development of sepsis, organ dysfunction, shock or coagulation disorders.

To avoid future adverse events, the initiation of antibiotic treatment must be well timed. The use of biomarkers can help to identify patients that require antibiotic treatment.

Procalcitonin is a well-known biomarker for the diagnosis of bacterial infections. Several clinical studies deal with the antibiotic stewardship in the ED-setting based on cut-off values of PCT for patients with infections or suspected infections of the respiratory tract. In such studies, the initiation of antibiotic treatment was discouraged up to a PCT level of 0.25 ng/ml and patients with less than 0.25 ng/ml of PCT were identified to have no clinically relevant bacterial infections.

For example, PCT has been described as a marker for the guidance of antibiotic therapy in treating patients with community-acquired pneumonia[40,41] or patients with unspecific complaints (WO 2011/110565). EP2320237 teaches an in vitro method for the diagnosis and treatment guidance of a bacterial infection in patients suffering from an acute ischemic or hemorrhagic stroke comprising the determination of PCT. However, these studies fail to teach the use of PCT as a biomarker in the relevant patient group of those having one or more comorbidities comprising an impaired innate immune response and suspected of having an infection, or to provide specific guidance on antibiotic treatment options, such as initiation or change of therapy or particular modes of administration.

Of note, is that patients with in impaired innate immune response, which may be due to the presence of a comorbidity, may require different criteria for antibiotic therapy guidance, such as different PCT cut-off levels, indicating the initiation or change in an antibiotic treatment, or different therapy recommendations, such as the particular mode of antibiotic administration. Clinicians are faced with additional challenges in determining at which time point, or other biological condition of a patient, antibiotics are to be administered or their use modified (eg escalated), in particular when the subject exhibits one or more conditions with an impaired innate immune response that may lead to variation in established PCT cut-off levels for patients without such additional complicating disorders.

In light of the prior art, a serious need exists in the field of treating patients with an impaired innate immune response suspected of having an infection, in particular sepsis, for additional and/or improved means for antibiotic therapy selection, guidance, stratification and/or control.

SUMMARY OF THE INVENTION

In light of the difficulties in the prior art, the technical problem underlying the present invention is the provision of alternative and/or improved means for antibiotic therapy guidance, stratification and/or control in a patient with an impaired innate immune response suspected of having an infection and/or displaying symptoms thereof, in particular symptoms of an infectious disease.

The present invention therefore seeks to provide a method, kit and further means for antibiotic therapy guidance, stratification and/or control in a patient suspected of having an infection, as well as a pharmaceutical composition comprising one or more antibiotic agents for use in the treatment of a patient suspected of having an infection. One object of the invention is therefore the use of a biomarker or combination of biomarkers and potentially one or more clinical scores to identify patients requiring the initiation or a change of an antibiotic treatment.

The solution to the technical problem of the invention is provided in the independent claims. Preferred embodiments of the invention are provided in the dependent claims.

The invention therefore relates to a method for antibiotic therapy guidance, stratification and/or control in a patient with an impaired innate immune response and suspected of having an infection, the method comprising:
 providing a sample from said patient, and
 determining a level of PCT or fragment(s) thereof in said sample,
 wherein the level of PCT or fragment(s) thereof in said sample is indicative of whether an initiation or a change of an antibiotic treatment is required.

In a preferred embodiment, the invention relates to a method for antibiotic therapy guidance, stratification and/or control in a patient with one or more comorbidities comprising an impaired innate immune response and suspected of having an infection, the method comprising:

provide a sample from said patient, and determining a level of PCT or fragment(s) thereof in said sample, wherein the level of PCT or fragment(s) thereof in said sample is indicative of whether an initiation or a change of an antibiotic treatment is required.

The method of the invention provides a very useful measure for medical personnel encountering a patient, who has an impaired innate immune response and who is suspected of having an infection due to the presence of symptoms of an infectious disease or of a sepsis, to decide whether an (immediate) antibiotic treatment is required. The method is objective and fast, providing a high degree of security to the person in charge of therapeutic measures to make the correct treatment decision. PCT can provide such information as a sole biomarker employed in a diagnostic method or in a method for therapy guidance and stratification that may be performed upon first encountering a patient displaying symptoms of an infectious disease. It was, as such, a surprising and beneficial discovery that PCT is a suitable marker for establishing whether initiation or a change of an antibiotic treatment is required in a patient with an impaired innate immune response and suspected of having an infection.

It represents a significant problem for medical personnel and physicians who encounter patients with an impaired innate immune response, for example due to a comorbidity that is affecting the innate immune response, whether an antibiotic treatment should be initiated or changed. Impairment of the innate immune response, especially in the context of comorbidities that alter the innate immune response in a way to act less efficiently against danger signals or pathogens, may change the decision criteria for the initiation or change of an antibiotic treatment, which is why known antibiotic treatment guidance criteria as described in the prior art may not be sufficient for antibiotic treatment guidance in this specific group of patients.

In a preferred embodiment of the invention, the impaired innate immune response is or refers to an impairment of immune cells of the innate immune system, such as an impaired response and/or function one or more immune cells of the innate immune system.

However, an early initiation of antibiotic treatment may be particularly important in the specific patient group of the present invention, because the impairment of the innate immune response makes these patients extremely vulnerable to infections. Therefore, it is a great advantage of the method of the present invention that it enables antibiotic therapy guidance based on defined decision criteria for this specific patient population.

Furthermore, the presence of a comorbidity comprising an impaired innate immune response may affect the basal level of PCT even in the absence of an infection. Therefore, until now medical personnel or physicians that are faced with a patient with an impaired innate immune response, which may be due to a comorbidity comprising an impaired innate immune response, were uncertain about how to interpret elevations of PCT over the baseline level with respect to the decision of initiating or changing an antibiotic treatment, because different criteria may be applied to this patient group as compared to patients without a known impairment of the innate immune response. This problem is now solved now by the method of the present invention and the preferred embodiments.

The present invention employs potentially a range of biomarkers (proADM, PCT, lactate, C-reactive protein (CRP)) and clinical severity scores (SOFA and qSOFA) in order to assess (i) initial requirement for initiation or change in antibiotic treatment, (ii) prediction of a positive blood culture, (iii) development of severe sepsis, preferably within 48 hours from presentation of the patient and or isolation of sample, and/or (iv) disease severity as assessed by 28 day mortality rate.

Physicians or medical personnel who encounter patients with impaired innate immune responses that are suspected of having an infection, for example in an emergency department or a primary care unit, but also in any other setting, such as during a home visit by the doctor or medical personnel or in an ambulance or at the site of an emergency, may employ the method of the present invention in some embodiments in a point of care format, preferably in an emergency department or primary care unit. This represents a great advantage over other biomarker tests that require sample analysis in a laboratory, requiring much more time so that a biomarker-based treatment decision can only be taken after several hours or even days. In contrast, the method of the present invention can be performed on site, in the place where the patient is first seen by the person in charge of taking first treatment measures, such as in an emergency department, primary care unit or even an ambulance vehicle.

The method is useful to decide whether a patient suspected of having an infection should receive antibiotic treatment, or whether an ongoing antibiotic treatment should be continued or changed or stopped. Furthermore, based on the level of procalcitonin or fragments thereof it can be judged whether a patient is a high risk patient that should be under intense medical observation, wherein an antibiotic treatment should be initiated or modified, or whether the patient is a low risk patient with a stable or even improving health state that might not require an antibiotic treatment or a change of the antibiotic treatment.

Accordingly, the method of the present invention can help to improve the treatment decisions to be taken upon medical personnel encountering a patient. The method of the invention can discriminate high risk patients, who are more likely to require an initiation or change of an antibiotic therapy, from low risk patients, whose health state is stable or even improving, even without initiation or change in the antibiotic therapy.

In further embodiments of the invention, a level of PCT or fragment(s) thereof in a sample equal to or above 0.05 ng/ml, preferably equal to or greater than 0.1 ng/ml, more preferably equal to or above 0.12 ng/ml, indicates that an initiation or a change of an antibiotic treatment is required. In embodiments of the invention, wherein the level of PCT or fragments thereof does not indicate that an initiation or a change of an antibiotic treatment is required, the patient may be discharged, discharged from ICU or any hospital or clinical setting, or not hospitalized.

The cut-off values of the protein level of PCT or fragment(s) thereof or of other biomarkers, disclosed herein refer preferably to measurements in a sample obtained from a patient by means of the Thermo Scientific BRAHMS KRYPTOR assay. Accordingly, the values disclosed herein may vary to some extent depending on the detection/measurement method employed or vary due to different automated systems, and the specific values disclosed herein are intended to also read on the corresponding values determined by other methods.

In other embodiments, wherein the level of PCT or fragments thereof indicates that an initiation or a change of an antibiotic treatment is required, the patient may be hospitalized or admitted to ICU. ICU admission may by considered in particular if the patient is already hospitalized. In another alternative embodiment, where the level of PCT or fragments thereof indicates that an initiation or a change of an antibiotic treatment is not required, the patient may be discharged from a hospital or a hospital setting with the requirement of non-intravenous antibiotics (oral antibiotics) or no antibiotics.

A particular advantage of the method of the present invention is that patients who are suspected of having an invention can be stratified with respect to the required therapy. The stratified patient groups may include patients that require an initiation or change of an antibiotic treatment and patients that do not require antibiotic treatment or a change of an ongoing treatment. Furthermore, it may be possible to decide on the basis of the level of procalcitonin or fragments thereof what kind of antibiotic treatment may be required, for example with respect to the antibiotic agent or combination of the antibiotic agent to be administered, the rout or routes of administration for the respective antibiotic agents and the treatment regime, such as single or repeated or multiple administrations and potentially the intervals of administration.

Accordingly, the method of the invention can help to avoid unnecessary use of antibiotics. This could result in a more efficient use of antibiotics, preferably intravenously applied antibiotics, which would not only avoid unnecessary costs but also the development of antibiotic resistance, which are promoted by the unnecessary use of antibiotic agents. Furthermore, it can be reliably decided, which patients should be monitored and potentially hospitalized during antibiotic treatment after encounter of the medical personnel, for example in an emergency department of a hospital, and which patients can be discharged, because they do not require tight monitoring. Consequently, the respective hospital or medical institution could be managed more efficiently as only patients that require antibiotic therapy may have to stay for further treatment, while the other patients may be discharged. This would also lead to significant benefits from avoided costs for unnecessary measures that would otherwise be applied to low risk patients that do not require antibiotic treatment.

According to the method of the invention the patients have an impaired innate immune response. Due to an under or overperforming innate immune response those patients show an abnormal first line of defense against invading pathogens and represent a high risk group to infections and associated complications, such as for example shock, organ dysfunction or coagulation disorder (e.g. Disseminated Intravascular Coagulation-DIC).

In a preferred embodiment, the patients of the method of the present invention have not yet been diagnosed as suffering from an infection or an infectious disease. However, the patient is suspected of having an infection as he may display symptoms or signs of an infection.

Furthermore, although the patient has not yet been diagnosed as having an infectious disease or sepsis, the patient may already receive antibiotic treatment, such as an oral antibiotic agent.

The method of the present invention can therefore be used for deciding whether a subject presenting with symptoms or signs of an infection should receive an antibiotic treatment. Symptoms of an infection are very diverse depending on the organ system that may be affected by the infection. However, such symptoms are well defined and known to a skilled person, such as medical personnel working in emergency department, a primary care unit, a hospital or a similar institution. General signs of an infectious disease and also of sepsis comprise, without limitation, fever, elevated body temperature, body temperature above 38° C., runny nose, cough, headache, fatigue, body aches, nausea, vomiting, diarrhea, fever, chills, abdominal pain, heart rate higher than 90 beats a minute, respiratory rate higher than 20 breaths a minute, significantly decreased urine output, abrupt change in mental status, decrease in platelet count, difficulty breathing, abnormal heart pumping function or low blood pressure.

In another embodiment of the invention, the subject displays symptoms of an infection or systemic infection such as sepsis.

The determined levels of procalcitonin or fragments thereof indicate whether an initiation of an antibiotic treatment or a change of the ongoing antibiotic treatment is required. On the basis of the method of the present invention it can be decided, whether a treatment should be initiated, changed or continued or whether no antibiotic treatment is required.

In the context of the present invention, a change in the antibiotic treatment of a patient can involve a change in the dose, the administration route or regime or other parameters of antibiotic treatment, while the changed treatment may still encompass the same one or more antibiotic agents, which have been used initially. Furthermore, a change in the antibiotic treatment may also and potentially additionally relate to a change in the one or more antibiotic agents use for treating the patient. A change can therefore relate to the addition of a further antibiotic agent or to the replacement of one or more antibiotic agents by one or more other agents.

In preferred embodiments, a change in the antibiotic treatment refers to the initiation of an antibiotic treatment in a patient that does not receive antibiotic treatment. Further, a change in the antibiotic treatment may relate to an escalation of antibiotic treatment. For example, the escalation may be with respect to the route of administration, such as, for example, initiation of intravenous antibiotic treatment in a patient receiving oral and/or topical antibiotic treatment, wherein intravenous antibiotic treatment may be administered instead or in addition to the previous antibiotic treatment. An escalation in antibiotic therapy preferably occurs when the level of PCT or fragments thereof indicates that an initiation or a change of an antibiotic treatment is required.

Additionally, a change in the antibiotic treatment may relate to a de-escalation of antibiotic treatment with respect to the route of administration. For example, de-escalation may relate to replacing intravenous antibiotic treatment with oral and/or topical administration of antibiotic treatment, or stopping antibiotic treatment. Furthermore, a change in the antibiotic treatment may also relate to a change of the setting of administration of an antibiotic treatment. For example, a change of antibiotic treatment in the sense of an escalation may relate to the administration of antibiotic treatment in a hospital setting to a patient that was not hospitalized previous to the change of antibiotic treatment, or administration of antibiotic treatment in an ICU setting to a patient that was not an ICU-patient previous to the change of antibiotics. Moreover, in the sense of an escalation or de-escalation of antibiotic treatment may relate to the administration of antibiotic treatment or change or discontinuation of antibiotic treatment in a hospital setting to a patient that was hospitalized such as for example the patient was already admitted to an Intensive Care Unit or any other clinical setting. Herein, the terms antibiotic treatment and antibiotic therapy are used interchangibly. A change in antibiotic treatment may in some embodiments comprise the administration of additional or fewer antibiotic agents, depending on the outcome of the PCT measurement. A de-escalation in antibiotic therapy preferably occurs when the level of PCT or fragments thereof indicates that a subject does not indicate an increased risk of an infection requiring additional antibiotic treatment.

In some embodiments, the antibiotic therapy guidance, stratification and/or control preferably involves the prognosis of the success or efficacy of the ongoing antibiotic therapy, also with respect to the likelihood of a future adverse event.

According to the present invention, the term "indicate" in the context of "indicative of whether an initiation or a change of an antibiotic treatment is required" is intended as a measure of likelihood that initiation of an antibiotic treatment or a change of an ongoing antibiotic treatment may be required. Preferably, the "indication" of the initiation or change in the antibiotic treatment being required is intended to refer to an increased likelihood that the patient suffers from an infection that can be successfully treated by administration of suitable antibiotic agents leading to an improvement of the health status of the patient. On the other hand, the level of procalcitonin or fragments thereof can be indicative of the fact that an antibiotic treatment may not help to improve the state of the patient because although the patient is suspected of having an infection, administration of antibiotic may not lead to an improvement of the health status.

In the context of the present invention, an indication of a requirement of initiating or changing an antibiotic treatment, such as for example changing one or more antibiotic agents used in the antibiotic therapy of a patient suffering from an infectious disease, may be associated with an increased likelihood of the occurrence of a future adverse event in the health of the patient. The indication of an initiation or change of an antibiotic therapy may be intended as an assessment of the efficacy of the intended antibiotic treatment, and is typically not to be construed in a limiting fashion as to point definitively to the absolute success or failure of antibiotic treatment, which may be display in a successive improvement of the health status of a patient.

Keeping the above in mind, the method of the invention represents a very reliable procedure with respect to determining whether an antibiotic treatment initiation or change is required, in particular when using the cut-off values disclosed herein.

According to a preferred embodiment of the method of the invention, the provided sample was isolated from the patient within 12 hours from first contact with medical personnel, preferably within 6 hours, 2 hours, 1 hour, or more preferably within 30 minutes from first contact with medical personnel.

In a preferred embodiment of the invention, the provided sample was isolated from the patient within 12 hours after presentation of symptoms of an infection and/or symptoms of sepsis to medical personnel, preferably within 6 hours, 2 hours, 1 hour, or more preferably within 30 minutes after presentation of said symptoms to medical personnel.

The time point of the first contact between the patient and the medical personnel is defined as the time when the medical personnel first examines a patient that has contacted the medical personnel or has been presented to the medical personnel. This may also be the time point when symptoms of an infection or a sepsis may be presented. An examination may relate to a physical examination, medical examination, or clinical examination, which may be the process by which a medical professional investigates the body of a patient for signs of disease. It usually involves the taking of the medical history, the assessment of ongoing treatments and an account of the symptoms as experienced by the patient. Together with the medical history, the physical examination aids in determining the correct diagnosis and devising the treatment plan.

The time point when the medical professional becomes aware of the symptoms of a patients may also be the time point when the patient is identified as a patient suspected of having an infection. This time point may also be referred to as the reference time point or time point 0, to which time spans referred to in the context of the method of the invention relate. Ideally, the sample, in which the level of PCT or fragments thereof should be determined, should be isolated as soon as possible after identifying a patient as being suspected of having an infection, to be able to receive the result of the sample analysis very quickly and therefore take an PCT-based treatment decision very quickly. It may be critical for the successful outcome of a treatment of a patient suspected of having an infection or a sepsis to initiate the correct treatment very quickly after recognizing the patient's symptoms. Therefore, it is preferable that in the context of the present invention, the sample is isolated within 12 hours, preferably, 11, 10, 9, 8, 7, 6, 5, 4, 3, 2.5, 2, 1.5, 1, 0.9, 0.8, 0.7, 0.6, 0.5, 0.4, 0.3, 0.2, 0.1 hours or immediately after first contact and/or presentation of symptoms to medical personnel. Preferably, the sample can be analyzed directly at the site of sample isolation, for example in the emergency department, a point of care unit or an ambulance, by using a point of care assay that may be automated or semi-automated and provides a result within a very short time to the medical professional in charge of taking a treatment decision. In this way, the time for getting the required information for making a treatment decision on the basis of the present invention can be significantly reduce, which may be crucial for the success of the potentially initiated antibiotic treatment.

In a preferred embodiment, the antibiotic treatment is initiated or changed immediately upon provision of the result of the sample analysis indicating the level of PCT or fragments thereof in the sample. In further embodiments, the treatment may be initiated within 12 hours, preferably 11, 10, 9, 8, 7, 6, 5, 4, 3, 2.5, 2, 1.5, 1, 0.9, 0.8, 0.7, 0.6, 0.5, 0.4, 0.3, 0.2, 0.1 hours or immediately after receiving the result of the sample analysis.

Preferably, the patient presents in an emergency department or a primary care.

It is a great advantage of the method of the invention that is can be performed at the site of encounter of the patient and does not necessarily require a specified laboratory, which may consume time for transport and provision of the result. Furthermore, the treatment decision based on the method of the invention can be taken very quickly after encountering the patient in an ED or a primary care unit.

In a preferred embodiment the patient has one or more comorbidities which can be selected from the group comprising cardiovascular disease, atrial fibrillation, flutter, congestive heart failure, COPD, asthma, lung fibrosis, asbestosis, pulmonary disease, immunodeficiency, diabetes, renal disease, hypertension, stroke, transient ischemic attack (TIA), dementia, anemia, thrombosis, rheumatic disease, neuromuscular disease, malignancy or cancer.

In a more preferred embodiment the patient has one or more comorbidities which are linked to an impaired innate immune response and which can be selected from the group comprising metabolic disorder (obesity), diabetes, immunodeficiency, renal disease, hypertension, anemia, thrombosis, malignancy or cancer.

In a preferred embodiment the patient has one or more comorbidity comprising the impaired innate immune response, wherein the comorbidity comprising the impaired innate immune response is preferably selected from the group comprising metabolic disorder (obesity), diabetes, immunodeficiency, hypertension, renal disease, anemia, thrombosis, malignancy or cancer.

In a most preferred embodiment the patient has one or more comorbidities comprising hypertension, metabolic disorder (obesity), diabetes and anemia.

In one embodiment the patient has one or more comorbidities which are linked to an impaired innate immune response and which can be selected from the group comprising metabolic disorder (obesity), diabetes, immunodeficiency, renal disease, anemia, thrombosis, malignancy or cancer.

In one embodiment the patient has one or more comorbidities comprising metabolic disorder (obesity), diabetes and anemia.

In one embodiment, the patient has hypertension as a comorbidity, but has not experienced acute ischaemic or hemorrhagic stroke. In one embodiment, the patient has hypertension as a comorbidity, but has not experienced acute ischaemic or hemorrhagic stroke within the last 96, 72, 48 or 24 hours. In one embodiment, the patient has not had a stroke. In one embodiment, the patient does not have hypertension.

Patients who have experienced stroke, such as acute ischaemic or hemorrhagic stroke, are not directly relevant to the patient group of the present invention. The present invention seeks to assess relevant PCT values in patients with underlying and potentially chronic additional medical conditions (in addition to any suspected infection), thereby enabling improved assessment of necessary treatments and therefore improved treatment guidance. In some embodiments of the invention the patients are not acutely ill due to the comorbiditiy. In some embodiments the comorbidity is a chronic medical condition, i.e. without acute status. In a preferred embodiment of the invention, determining a level of PCT or fragment(s) thereof in said sample that is greater than the level of PCT or fragment(s) thereof in one or more control samples, such as in a group of healthy individuals, indicates that an initiation or a change of an antibiotic treatment is required.

In such preferred embodiments, it is possible to use control samples or control values having been generated by the testing control sample, such a preferably cohorts or other large numbers of subjects suffering from any given disease or a control group. Appropriate statistical means are known to those skilled in the art for analysis and comparison of such data sets. Control samples for positive controls (such as disease sufferers) or negative controls (from healthy subjects) may be used for reference values in either simultaneous of non-simultaneous comparison.

The cut-off values of the protein level of procalcitonin or fragments thereof refer most preferably to measurements in a plasma sample or serum sample or blood sample (full blood sample) obtained from a patient. Accordingly, the values disclosed herein may vary to some extent depending on the detection/measurement method employed, and the specific values disclosed herein are intended to also read on the corresponding values determined by other methods.

In one embodiment the invention additionally comprises informing the patient of the results of the method described herein. In a further embodiment the invention additionally comprises initiation of an antibiotic treatment. Furthermore, the method may comprise a step of stratifying the patient into a specific therapy group, which is associated with a specific treatment regime, and optionally informing the patient about the result of the treatment stratification.

In a preferred embodiment of the method of the invention, a level of PCT or fragment(s) thereof is equal to or above 0.05 ng/ml, preferably equal to or above 0.1 ng/ml, more preferably equal to or above 0.12 ng/ml indicates that an initiation or a change of an antibiotic treatment is required.

In a preferred embodiment of the method of the invention, a level of PCT or fragment(s) thereof is equal to or above 0.05 ng/ml, or above 0.1 ng/ml, more preferably equal to or above 0.12 ng/ml, or above 0.15 ng/ml, or above 0.17 ng/ml or above 0.2 ng/ml indicates that an initiation or a change of an antibiotic treatment is required.

In preferred embodiments, a level of PCT or fragments thereof is equal or above 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required.

In further embodiment of the invention, a level of PCT or fragments thereof with a concentration in the range of 0.05-0.4, 0.05-0.35, 0.05-0.3, 0.05-0.29, 0.05-0.28, 0.05-0.27, 0.05-0.26, 0.05-0.25, 0.05-0.25, 0.06-0.24. 0.07-0.23, 0.08-0.22, 0.09-0.21, 0.10-0.20, 0.11-0.19, 0.12-0.18, 0.13-0.17, or 0.14-0.16 ng/ml indicates that an initiation or a change of an antibiotic treatment is required.

In further embodiments, a level of PCT or fragments thereof equal to or above 0.17 ng/ml is indicative of the development of severe sepsis within 48 hours of presentation of the sample and/or isolation of the sample.

It was surprising that based on the level of below 0.25 ng/ml of PCT or fragments thereof it may be possible to confidently predict the likelihood of success of an antibiotic treatment to be initiated.

It is a great advantage of the method of the present invention that based on the level of procalcitonin or fragments thereof further treatment steps and decisions can be taken. If the level of procalcitonin equal to or above 0.05 ng/ml, preferably equal to or above than 0.1 ng/ml, more preferably equal to or above 0.12 ng/ml, this indicates that an antibiotic treatment should be initiated or that an ongoing antibiotic treatment should be modified or changed. Furthermore, it can be determined that the patient is a high risk patient that requires tight medical supervision and potentially additional treatment measures. On the other hand, if the level of procalcitonin or fragments thereof ins said sample is below 0.05 ng/ml, preferably below 0.1 ng/ml, more preferably below 0.12 ng/ml, this may indicate that the patient is not at a high risk infectious disease patient requiring antibiotic treatment a tight medical supervision. The patient may recover without further measures requiring medical supervision and may be discharged from the medical institution.

In a preferred embodiment the comorbidity comprising the impaired innate immune response is metabolic disorder (obesity) and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is diabetes and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is hypertension and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is renal disease and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is thrombosis and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is malignancy and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is cancer and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23 or 0.24 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is immunodeficiency and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

In a preferred embodiment the comorbidity comprising the impaired innate immune response is anemia and a level of PCT or fragments thereof equal or above 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 or 0.4 ng/ml indicates that an initiation or a change of an antibiotic treatment is required, or a level of PCT or fragments thereof in the range of 0.05-0.4, 0.05-0.35, 0.05-0.3, 0.05-0.29, 0.05-0.28, 0.05-0.27, 0.05-0.26, 0.05-0.25, 0.06-0.24. 0.07-0.23, 0.08-0.22, 0.09-0.21, 0.10-0.20, 0.11-0.19, 0.12-0.18, 0.13-0.17, 0.14-0.16 ng/ml indicates that an initiation or a change of an antibiotic treatment is required.

The present invention also employs the further assessment with or without additional biomarkers (for example pro-ADM, lactate, C-reactive protein, Interleukin-6, Histone H2A, Histone H2B, Histone H4, Neutrophil Gelatinase-Associated Lipocalin, pro-Endothelin-1, alpha-1-Antitrypsin, sICAM-1, IP-10) and clinical scores (for example SOFA, qSOFA, APACHE II, SAPS II) of: (i) initial requirement for initiation or change in antibiotic treatment, (ii) prediction of a positive blood culture, (iii) development of severe sepsis, and/or (iv) disease severity as assessed by 28 day mortality rate.

In a preferred embodiment, the method of the invention comprises additionally determining in a sample from said patient a level of at least one further biomarker, determining at least one clinical parameter and/or determining at least one clinical score.

In preferred embodiments, the at least one further biomarker is selected from the group comprising pro-ADM, lactate, C-reactive protein, Interleukin-6, Histone H2A, Histone H2B, Histone H4, Neutrophil Gelatinase-Associated Lipocalin, pro-Endothelin-1, alpha-1-Antitrypsin, sICAM-1 and IP-10.

In preferred embodiments, the at least one further biomarker is selected from the group comprising proADM, ADM, CRP and lactate.

In preferred embodiments, the at least one clinical parameter is selected from the group comprising blood pressure, body temperature, body weight, body mass index, age and gender.

In preferred embodiments, the at least one clinical score is selected from the group comprising SOFA score, qSOFA score, APACHE II and SAPS II score.

Further biomarkers, clinical parameters and/or clinical scores that might be used in the context of the present invention are known to the person skilled in the art.

According to a further preferred embodiment, the method additionally comprises
- determining a level of at least one additional biomarker or fragment(s) thereof in a sample from said patient, and/or
- determining at least one clinical score, and/or
- determining at least one clinical parameter
- wherein the level of the at least one additional biomarker and/or the at least one clinical score and/or at least one clinical parameter, and the level of PCT or fragment(s) thereof is indicative of whether an initiation or a change of an antibiotic treatment is required.

In a further preferred embodiment of the invention the sample for determining PCT or fragment(s) thereof is a bodily fluid, preferably selected from the group consisting of a blood sample, a serum sample, a plasma sample and/or a urine sample.

The sample for determining PCT or fragment(s) thereof and the sample for determining the at least one additional biomarker or fragment(s) thereof may be the same sample or different samples.

In a further embodiment of the invention, said patient has not yet received antibiotic treatment. In another embodiment of the invention, said patient has not yet received antibiotic treatment of the suspected infection. In a further embodiment of the invention, said patient has not yet received antibiotic treatment before first presentation at the emergency department or primary care unit or similar clinical sites.

According to a further preferred embodiment, said patient is receiving antibiotic treatment and the change of an antibiotic treatment comprises a change in the route of administration of the antibiotic treatment. Preferably, the patient is receiving oral antibiotic treatment. Furthermore, the route of administration after change of the antibiotic treatment preferably is intravenous.

This embodiment represents a surprising and beneficial aspect of the invention, whereby by through PCT measurement in the defined patient population, preferably of a single sample and/or at a single time point, antibiotic therapy can be intensified, for example by administering antibiotics intravenously, thereby enabling an effective enhancement of therapy at an early time point without the need for extended periods of observation or allowing risk to develop. The practical benefits to practitioners of assessing proADM levels and instigating e.g. intravenous therapy based on a single marker value is significant. Conversely, being able to determine when intensified therapy is not necessary, for example by determining lower levels of PCT, as described herein, represents effective means of avoiding more cost intensive and difficult procedures.

In a further preferred embodiment, the change of an antibiotic treatment comprises a change of the route of administration of an ongoing antibiotic treatment.

In a further preferred embodiment, the change of an antibiotic treatment consists of a change of the route of administration of an ongoing antibiotic treatment.

In preferred embodiments of the method of the invention, the antibiotic treatment is administered in combination with one or more medical treatments or therapeutic measures, such as, for example, organ therapy, supplemental oxygen, intravenous fluids, corticosteroids, vasopressor, mechanical ventilation, non-invasive ventilation, renal placement therapy or continuous positive airway pressure (CPAP).

In preferred embodiments of the invention, the patient is suspected of having an infection or has an infection, wherein the infection or the suspected infection may be associated with a positive blood culture, a pulmonary infection, an upper airway infection, a urinary tract infection, a skeletal or joint infection, a skin infection, a soft tissue infection, a CNS infection, an abdominal infection and/or an infection of unknown origin and/or a foreign object infection.

In preferred embodiments of the invention, the patient has a comorbiditiy and is suspected of having an infection or has an infection, wherein the infection or the suspected infection may be associated with one or more local infections selected from the group comprising a pulmonary infection, an upper airway infection, a urinary tract infection, a skeletal or joint infection, a skin infection, a soft tissue infection, a CNS infection, an abdominal infection, an infection of unknown origin and/or a foreign object infection.

In preferred embodiments of the invention, the patient has a comorbiditiy comprising an impaired immune response and is suspected or has an infection, wherein the infection may be associated with one or more local infections selected from the group comprising a pulmonary infection, an upper airway infection, a urinary tract infection, a skeletal or joint infection, a skin infection, a soft tissue infection, a CNS infection, an abdominal infection, an infection of unknown origin and/or a foreign object infection.

In preferred embodiments of the invention, the patient has a comorbiditiy comprising an impaired immune response selected from the group comprising hypertension, anemia, metabolic disorder (obesity) or diabetes and is suspected or has an infection, wherein the infection may be associated with one or more local infections selected from the group comprising a pulmonary infection, an upper airway infection, a urinary tract infection, a skeletal or joint infection, a skin infection, a soft tissue infection, a CNS infection, an abdominal infection, an infection of unknown origin and/or a foreign object infection.

The present invention further relates to a pharmaceutical composition comprising one or more antibiotic agents for use in the treatment of a patient with an impaired innate immune response and suspected of having an infection, wherein the patient is administered said composition after being identified by the method of the present invention as requiring an initiation or a change of an antibiotic treatment due to the levels of PCT or fragment(s) thereof in a sample obtained from said patient.

In another embodiment the present invention relates to a pharmaceutical composition comprising one or more antibiotic agents for use in the treatment of a patient with one or more comorbidities comprising an impaired innate immune response and suspected of having an infection, wherein the patient is administered said composition after being identified by the method of the present invention as requiring an initiation or a change of an antibiotic treatment due to the levels of PCT or fragment(s) thereof in a sample obtained from said patient.

Preferably, the administration of the pharmaceutical composition of the invention is initiated within 180 minutes, preferably within 120 minutes, more preferably within 60 minutes or immediately after determining the level of PCT or fragment(s) thereof in said sample.

In a preferred embodiment of the pharmaceutical composition of the invention, the composition of the invention is administered to the patient repeatedly and over a certain treatment period.

Furthermore, PCT and fragment(s) thereof is determined one or more times during the treatment period with the composition of the invention. PCT and fragment(s) thereof may be determined during treatment with the pharmaceutical composition of the invention for monitoring of treatment success and/or disease progression.

Preferably, the pharmaceutical composition of the invention is administered in combination with other treatments, such as for example treatment of comorbidities or treatments of the symptoms that different from an antibiotic treatment. In particular, the pharmaceutical composition of the invention is administered in combination with symptomatic treatments of skin infections, urinary tract infections and the like.

Preferably, the patient receives intravenous administration of the composition of the invention. Alternatively, the patient may receive intravenous and oral administration of one or more compositions.

The present invention further relates to a kit for carrying out the method for antibiotic therapy guidance, stratification and/or control in a patient suffering from a comorbidity and suspected of having an infection, comprising
    detection reagents for determining the level PCT or fragment(s) thereof, and
    reference data, such as a reference level, corresponding to a level of PCT or fragment(s) thereof in said sample equal to or above 0.05 ng/ml, preferably equal to or above 0.1 ng/ml, more preferably equal to or above 0.12 ng/ml, wherein said reference data is preferably stored on a computer readable medium and/or employed in the form of computer executable code configured for comparing the determined levels of PCT or fragment(s) thereof, and optionally additionally the determined levels of ADM or fragment(s) thereof, to said reference data.

The present invention also relates to a method for (i) determining an initial requirement for initiation or change in antibiotic treatment, (ii) predicting a positive blood culture, (iii) predicting the development of severe sepsis, and/or (iv) predicting disease severity as potentially assessed by 28 day mortality rate, in a patient with an impaired innate immune response and suspected of having an infection, the method comprising:

providing one or more sample(s) from said patient,
    determining a level of PCT or fragment(s) thereof in said one or more samples, and
    optionally determining a level of one or more additional biomarker(s), such as pro-ADM, lactate, C-reactive protein (CRP), and/or one or more clinical scores, such as SOFA, qSOFA or SAPS II,
    wherein the level of PCT or fragment(s) thereof and optionally the level of the one or more additional biomarker(s) and/or the clinical scores is indicative of (i) whether an initiation or a change of an antibiotic treatment is required, (ii) a positive blood culture, (iii) the development of severe sepsis and/or (iv) disease severity as potentially assessed by 28 day mortality rate.

Surprisingly, the present invention enables identification of patients that have clinically relevant bacterial infections and require antibiotic treatment by performing the method of the invention using a previously unknown cut-off of PCT of below 0.25 ng/ml on patients that suffer from a comorbidity comprising an impaired innate immune response that present in an emergency department with symptom of an infection or an infectious disease.

Furthermore, the present invention may be useful to predict the development of severe Sepsis within 48 hours of arrival at the emergency department.

According to a further preferred embodiment of the invention, said patient is receiving antibiotic treatment and the change of an antibiotic treatment comprises or consists of a change in the route of administration of the antibiotic treatment. Preferably, the patient is receiving topical or oral antibiotic treatment. Furthermore, the route of administration after change of the antibiotic treatment preferably is an intravenous application of antibiotics.

In a further preferred embodiment of the invention, the change of an antibiotic treatment comprises a change of the route of administration of an ongoing antibiotic treatment.

In a further preferred embodiment of the invention, the change of an antibiotic treatment consist of a change of the route of administration of an ongoing antibiotic treatment.

Preferred organ dysfunctions that may be determined in the context of the method of the invention relate to, without limitation, one or more of neurological dysfunction, cardiovascular dysfunction, respiratory dysfunction, renal dysfunction, hepatic dysfunction, hematological dysfunction and/or metabolic acidosis.

In further embodiments of the method described herein, the method additionally comprises a molecular analysis of a sample from said patient for detecting an infection. The sample used for the molecular analysis for detecting an infection preferably is a blood sample. In a preferred embodiment the molecular analysis is a method aiming to detect one or more biomolecules derived from a pathogen. Said one or more biomolecule may be a nucleic acid, protein, sugar, carbohydrates, lipid and or a combination thereof such as glycosylated protein, preferably a nucleic acid. Said biomolecule preferably is specific for one or more pathogen(s). According to preferred embodiments, such biomolecules are detected by one or more methods for analysis of biomolecules selected from the group comprising nucleic acid amplification methods such as PCR, qPCR, RT-PCR, qRT-PCR or isothermal amplification, mass spectrometry, detection of enzymatic activity and immunoassay based detection methods. Further methods of molecular analysis are known to the person skilled in the art and are comprised by the method of the present invention.

The present invention further relates to a pharmaceutical composition comprising one or more antibiotic agents for use in the treatment of a patient suspected of having an infection, wherein the patient is administered said composition after being identified by the method of the present invention as requiring an initiation or a change of an antibiotic treatment due to the levels of PCT or fragment(s) thereof in a sample obtained from said patient.

Preferably, the administration pharmaceutical composition of the invention is initiated within 180 minutes, preferably within 120 minutes, more preferably within 60 minutes or immediately after determining the level of PCT or fragment(s) thereof in said sample.

In a preferred embodiment of the pharmaceutical composition of the invention, the composition of the invention is administered to the patient repeatedly and over a certain treatment period. For example, the antibiotic treatment may be ongoing for several hours, days or weeks, wherein the antibiotics may be administered continuously, for example by i.v. infusion, or repeatedly, for example by oral administration or injection or topical application, wherein the intervals of administration may vary between one or more hours, days or weeks, depending on the state of the patient and/or the antibiotic agent(s) and formulations to be administered.

Preferably, the pharmaceutical composition of the invention is administered in combination with other treatments, such as for example treatment of comorbidities or treatments of the symptoms that are different from an antibiotic treatment. In particular, the pharmaceutical composition of the invention is administered in combination with symptomatic treatments of skin infections, urinary tract infections and the like.

Preferably, the patient receives intravenous administration of the composition of the invention. Alternatively, the patient may receive intravenous and oral administration of one or more compositions.

The present invention further relates to a kit for carrying out the method of the invention, comprising
  detection reagents for determining the level procalcitonin or fragment(s) thereof, and
  reference data, such as a reference level, corresponding to a level of PCT or fragment(s) thereof in said sample equal to or above 0.05 ng/ml, preferably equal to or above 0.1 ng/ml, more preferably equal to or above 0.12 ng/ml, wherein said reference data is preferably stored on a computer readable medium and/or employed in the form of computer executable code configured for comparing the determined levels of procalcitonin or fragment(s) thereof, and optionally additionally the determined levels of PCT or fragment(s) thereof, to said reference data.

The detection reagents for determining the level of procalcitonin or fragment(s) thereof are preferably selected from those necessary to perform the method, for example antibodies directed to procalcitonin, suitable labels, such as fluorescent labels, preferably two separate fluorescent labels suitable for application in the KRYPTOR assay, sample collection tubes.

In one embodiment of the method described herein the level of procalcitonin or fragment(s) thereof and optionally PCT or fragment(s) thereof is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analysers.

The method according to the present invention can furthermore be embodied as a homogeneous method, wherein the sandwich complexes formed by the antibody/antibodies and the marker, e.g., the procalcitonin or a fragment thereof, which is to be detected remains suspended in the liquid phase. In this case it is preferred, that when two antibodies are used, both antibodies are labelled with parts of a detection system, which leads to generation of a signal or triggering of a signal if both antibodies are integrated into a single sandwich.

Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labelling components in a single immune-complex directly in the reaction mixture are detected, become possible.

For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of the procalcitonin protein or a fragment thereof, and/or the level of any further marker of the herein provided method are determined. In particular preferred aspects, the diagnostic device is KRYPTOR®.

In one embodiment of the method described herein the method is an immunoassay and wherein the assay is performed in homogeneous phase or in heterogeneous phase and can be run on automated systems.

In one embodiment of the method described herein a first antibody and a second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said PCT or fragments thereof to be detected, a measurable signal which permits detection of the resulting sandwich complexes in the measuring solution is generated.

In one embodiment of the method described herein the labelling system comprises a rare earth cryptate or chelate in combination with a fluorescent or chemiluminescent dye, in particular of the cyanine type.

In one embodiment of the method described herein, the method additionally comprises comparing the determined level of procalcitonin or fragment(s) thereof to a reference level, threshold value and/or a population average corresponding to procalcitonin or fragments thereof in patients who are suspected of having an infection or who display symptoms of sepsis, wherein said comparing is carried out in a computer processor using computer executable code.

The methods of the present invention may in part be computer-implemented. For example, the step of comparing the detected level of a marker, e.g. the procalcitonin or fragments thereof, with a reference level can be performed in a computer system. In the computer-system, the determined level of the marker(s) can be combined with other marker levels and/or parameters of the subject in order to calculate a score, which is indicative for the diagnosis, prognosis, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. primary care unit or ED) or it can be at a remote location connected via a computer network (e.g. via the internet, or specialized medical cloud-systems, optionally combinable with other IT-systems or platforms such as hospital information systems (HIS)). Typically, the computer-system will store the values (e.g. marker level or parameters such as age, blood pressure, weight, sex, etc. or clinical scoring systems such as SOFA, qSOFA, BMI etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician).

In one embodiment of the invention, a software system can be employed, in which a machine learning algorithm is evident, preferably to identify hospitalized patients at risk for sepsis, severe sepsis and septic shock using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of procalcitonin levels may be incorporated into appropriate software for comparison to existing data sets, for example procalcitonin levels may also be processed in machine learning software to assist in diagnosing or prognosing the occurrence of an adverse event.

The combined employment of procalcitonin or fragments thereof in combination with another biomarker such as CRP or lactate may be realised either in a single multiplex assay, or in two separate assays conducted on a sample form the patient. The sample may relate to the same sample, or to different samples.

Cut-off values and other reference levels of procalcitonin or fragments thereof in patients who are suspected of having an infection may be determined by previously described methods. For example, methods are known to a skilled person for using the Coefficient of variation in assessing variability of quantitative assays in order to establish reference values and/or cut-offs (George F. Reed et al., Clin Diagn Lab Immunol. 2002; 9(6):1235-1239).

Additionally, functional assay sensitivity can be determined in order to indicate statistically significant values for use as reference levels or cut-offs according to established techniques. Laboratories are capable of independently establishing an assays functional sensitivity by a clinically relevant protocol. "Functional sensitivity" can be considered as the concentration that results in a coefficient of variation (CV) of 20% (or some other predetermined % CV), and is thus a measure of an assays precision at low analyte levels. The CV is therefore a standardization of the standard deviation (SD) that allows comparison of variability estimates regardless of the magnitude of analyte concentration, at least throughout most of the working range of the assay.

Furthermore, methods based on ROC analysis can be used to determine statistically significant differences between two clinical patient groups. Receiver Operating Characteristic (ROC) curves measure the sorting efficiency of the model's fitted probabilities to sort the response levels. ROC curves can also aid in setting criterion points in diagnostic tests. The higher the curve from the diagonal, the better the fit. If the logistic fit has more than two response levels, it produces a generalized ROC curve. In such a plot, there is a curve for each response level, which is the ROC curve of that level versus all other levels. Software capable of enabling this kind of analysis in order to establish suitable reference levels and cut-offs is available, for example JMP 12, JMP 13, Statistical Discovery, from SAS.

Cut off values may similarly be determined for PCT. Literature is available to a skilled person for determining an appropriate cut-off, for example Philipp Schuetz et al. (BMC Medicine. 2011; 9:107) describe that at a cut-off of 0.1 ng/mL, PCT had a very high sensitivity to exclude infection. Terence Chan et al. (Expert Rev. Mol. Diagn. 2011; 11(5), 487.496) described that indicators such as the positive and negative likelihood ratios, which are calculated based on sensitivity and specificity, are also useful for assessing the strength of a diagnostic test. Values are commonly graphed for multiple cut-off values (CVs) as a receiver operating characteristic curve. The area under the curve value is used to determine the best diagnostically relevant CV. This literature describes the variation of CVs (cut-off values, that is dependent on the assay and study design), and suitable methods for determining cut-off values.

Population averages levels of procalcitonin or fragments thereof may also be used as reference values, for example mean procalcitonin population values, whereby patients that are suspected of having an infection of displaying symptoms of sepsis may be compared to a control population, wherein the control group preferably comprises more than 10, 20, 30, 40, 50 or more subjects.

In one embodiment of the invention, the cut-off level for PCT may be a value in the range of 0.01 to 100.00 ng/mL in a serum sample, when using for example the BRAHMS PCT-Kryptor Assay or automated systems such as for example the Cobas system by Roche or the Vidas System by BioMérieux or the Architect System by Abbott. In a preferred embodiment the cut-off level of PCT may be in the range of 0.01 to 100, 0.05 to 50, 0.1 to 20, or 0.1 to 2 ng/mL, and most preferably >0.05 to 0.5 ng/mL. Any value within these ranges may be considered as an appropriate cut-off value. For example, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95 or 100 ng/mL may be employed. In some embodiments, PCT levels for healthy subjects are approximately 0.05 ng/mL.

The present invention also relates to a method for antibiotic therapy guidance, stratification and/or control as well as diagnosis, prognosis, risk assessment and/or risk stratification of a subsequent adverse event in the health of a patient suffering from a comorbidity and suspected of having an infection, the method comprising
　providing a sample from said patient,
　determining a level of PCT or fragment(s) thereof in said sample, and
　wherein the level of PCT or fragment(s) thereof in said sample is indicative of whether an initiation or a change of an antibiotic treatment is required.

The present invention also relates to a method for antibiotic therapy guidance, stratification and/or control of a patient in a patient suffering from a comorbidity and suspected of having an infection, the method comprising providing a sample from said patient, determining a level of PCT or fragment(s) thereof in said sample, and wherein the level of PCT or fragment(s) thereof in said sample is indicative of whether an initiation or a change of an antibiotic treatment is required.

In another embodiment of the invention, the subject displays symptoms of sepsis.

All preferred embodiments and advantages of the methods of the present invention disclosed herein also apply to the pharmaceutical composition and the kit of the present invention. This also applies the other way around for the preferred embodiments and advantages of the pharmaceutical composition and the kit of the invention.

DETAILED DESCRIPTION OF THE INVENTION

The invention relates to a method for antibiotic therapy guidance, stratification and/or control in a patient with an impaired innate immune response and suspected of having an infection. As is evident from the data presented herein, the initiation or change of an antibiotic treatment is indicated by the level of procalcitonin or fragment(s) thereof, which provides information on potentially initiating or changing an antibiotic treatment.

As used herein, the "patient" or "subject" may be a vertebrate. In the context of the present invention, the term "subject" includes both humans and animals, particularly mammals, and other organisms.

As used herein, a primary care unit is a doctor's practice or a health care center where day-to-day primary healthcare may be given by a health care provider to a patient. Typically the provider acts as the first contact and principal point of continuing care for patients within a healthcare system, and coordinates other specialist care that the patient may need. Patients commonly receive primary care from professionals such as a primary care physician (for example a general practitioner or family physician), a nurse practitioner (such as an adult-gerontology nurse practitioner, family nurse practitioner, or pediatric nurse practitioner), or a physician assistant. Such a professional may also be a registered nurse, a pharmacist, a clinical officer.

In the context of the present invention, an emergency department (ED), also known as an accident and emergency department, emergency room (ER), emergency ward (EW) or casualty department, is a medical treatment facility specializing in emergency medicine, which involved the acute care of patients who present without prior appointment either by their own means or by that of an ambulance. Emergency departments are usually found in hospitals or other primary care centers.

In the context of the present invention, the term "innate immune response" refers to the reactions or responses mediated by the innate immune system. The innate immune system responds to stimulation by a pathogen in the context of an infection or to other danger signals that occur in an organism. The innate immune system is an important subsystem of the overall immune system that comprises cells and mechanisms that defend the host from infection by other organisms. The cells of the innate system may recognize and respond to pathogens and danger signals and provide immediate defense against infection, which is active before activation of the adaptive immune system, and is therefore called the first line of defense or an organism against invading pathogens.

The major functions of the innate immune system include recruiting immune cells to sites of infection through the production of chemical factors, including specialized chemical mediators, called cytokines; activation of the complement cascade to identify bacteria, activate cells, and promote clearance of antibody complexes or dead cells; identification and removal of foreign substances present in organs, tissues, blood and/or lymph, by specialized white blood cells; activation of the adaptive immune system, for example through a process known as antigen presentation; acting as a physical, chemical and/or biological barrier to infectious agents; initiation of inflammation.

Important components and mechanisms of the innate immune system comprise anatomical barriers of the body, the initiation of inflammation, innate immune cells and the complement system.

The immune cells of the innate immune system comprise natural killer cells, mast cells, eosinophils, basophils, macrophages, neutrophils, and dendritic cells. These cells can function within the immune system by identifying and eliminating pathogens that might cause infection. Furthermore, the cells of the innate immune system can contribute to the activation of the adaptive immune system.

Anatomical barriers include physical, chemical and biological barriers. The epithelial surfaces form a physical barrier that is impermeable to most infectious agents, acting as the first line of defense against invading organisms.

Inflammation is one of the first responses of the innate immune system to infection or irritation and is stimulated by the release of chemical factors by injured cells or by innate immune cells that recognize pathogens or other danger signals. Inflammation serves to prevent the spread of an infection, and to promote healing of any damaged tissue following the clearance of pathogens. The process of acute inflammation can be initiated by cells of the innate immune system already present in all tissues, mainly resident macrophages, dendritic cells, histiocytes, Kupffer cells, and mastocytes. These cells present receptors contained on the surface or within the cell, named pattern recognition receptors (PRRs), which recognize molecules that are broadly shared by pathogens but distinguishable from host molecules, collectively referred to as pathogen-associated molecular patterns (PAMPs). At the onset of an infection, burn, or other injuries, these cells can undergo activation (one of their PRRs recognizes a PAMP) and release inflammatory mediators responsible for the clinical signs of inflammation.

The complement system comprises of a number of small proteins found in the blood, in general synthesized by the liver, and normally circulating as inactive precursors (proproteins). When stimulated by a trigger, proteases in the complement system cleave specific proteins to release cytokines and initiate an amplifying cascade of further cleavages. The end result of this complement activation or complement fixation cascade is stimulation of phagocytes to clear foreign and damaged material, proxy inflammation to attract additional phagocytes, and activation of the cell-killing membrane attack complex. Over 30 proteins and protein fragments make up the complement system, including serum proteins, serosal proteins, and cell membrane receptors. At least three biochemical pathways activate the complement system, comprising the classical complement pathway, the alternative complement pathway, and the lectin pathway.

The term "impaired innate immune response" relates to a change in the innate immune response, which may be an overperformance and/or an underperformance of one or more components of the innate immune system, leading to an impaired innate immune response. Both, under- or overperformance of components of the innate immune response may lead to an imbalanced immune response, which my lead to a less efficient eradication of infectious agents or may lead to an overwhelming innate immune response, which may lead to pathological process and adverse events in the health of a patient. For example, septic shock can be associated with an overwhelming release of proinflammatory cytokines, which deteriorates the health status of a patient.

Many diseases or pathologies or comorbidities comprise an impairment or alteration of components of the innate immune system, which lead to an impaired innate immune response, which may be based on an overperformance or underperformance of the innate immune response. Some clinical conditions are characterized by a constant low-grade inflammatory state and constant activation of immune cells of the innate immune system which causes a densitization of the immune cells during antigenic exposure and a less efficient response to infectious stimuli respectively.

The person skilled in the art is aware of such pathologies. In the context of the present invention, diseases or comorbidities that are associated with an impaired innate immune response comprise, without limitation, metabolic disorder (obesity), diabetes, immunodeficiency, renal disease, hypertension, anemia, thrombosis, malignancy or cancer.

The patient as described herein has an infection or is suspected of having an infection. Whether or not infected, the patient may show symptoms of an infection.

Furthermore, the patient may have an impaired innate immune response. Furthermore the patient may have an impaired immune response associated with the cellular innate immunity. Furthermore, the patient may have one or more comorbidities. Furthermore, the patient may show symptoms of an infection and have a comorbidity that is associated with an impaired innate immune response. In the context of the invention, a comorbidity that is associated with an impaired innate immune response comprises an impaired innate immune response.

Furthermore, in some embodiments, the patient shows symptoms of an infection and has a comorbidity that is associated with an overperforming innate immune response. Overperformance of the innate immune response relates to an overwhelming innate immune reaction, which means that the reaction of the innate immune system is higher than in a healthy individual that does not suffer from the respective comorbidity.

Furthermore, in some embodiments, the patient shows symptoms of an infection and has a comorbidity that is associated with an underperforming innate immune response. Underperformance of the innate immune response relates to a impaired or weakened innate immune reaction, which means that the reaction of the innate immune system is weaker than in a healthy individual that does not suffer from the respective comorbidity.

In a preferred embodiment patients have one or more comorbidities which can be selected from the group comprising cardiovascular disease, atrial fibrillation, flutter, congestive heart failure, COPD, asthma, lung fibrosis, asbestosis, pulmonary disease, immunodeficiency, diabetes, renal disease, hypertension, stroke, transient ischemic attack (TIA), dementia, anemia, thrombosis, rheumatic disease, neuromuscular disease, malignancy or cancer.

In a more preferred embodiment patients have one or more comorbidities comprise (or are associated with) an impaired innate immune response and which can be selected from the group comprising metabolic disorder (obesity), diabetes, immunodeficiency, renal disease, hypertension, anemia, thrombosis, malignancy or cancer.

In a most preferred embodiment of the invention the patient has one or more comorbidities comprising an impaired innate immune response, wherein the comorbidity is selected from the group comprising hypertension, metabolic disorder (obesity), diabetes and anemia.

In a preferred embodiment of the invention the comorbidity comprising an impaired innate immune response refers to metabolic disorders, preferably obesity. Obese subjects or patients represent a risk group and are susceptible for infections. Different studies could show low-grade inflammatory conditions due to the action of pro-inflammatory cytokines and leptin which stimulates the chemotaxis of neutrophils, stimulates monocyte proliferation as well as the phagocytosis of macrophages. The constant pro-inflammatory stimulating effects may lead to a densitization of the innate immune cells which leads to an impaired innate immune defense during antigenic (e.g. bacterial pathogen) exposure (Falagas M. E. et al. Lancet Infect Dis. 2006 July; 6(7):438-46; Bandaru et al. Endocrinol Metab Synd 2013, Volume 2, Issue 2).

In a preferred embodiment of the invention the comorbidity comprising an impaired innate immune response refers to metabolic disorders, preferably Diabetes Type I or Type II. Hyperglycemia influences the host response including function of immune cells and regulation of cytokines. Subjects suffering from diabetes have an impaired cellular innate immune response and have an increased risk to acquire an infection. It was shown that constant activation of neutrophils and macrophages resulted in a decreased chemotaxis, decreased phagocytic performance with a reduced oxidative burst as soon as those cellular components of the innate immune system were stimulated by an infectious pathogen (Dryden M. et al. Clin Microbiol Infect 2015; 21: S27-S32; Rajagopalan S. Clinical Infectious Diseases 2005; 40:990-996; Geerlings S. E. et al. FEMS Immunology and Medical Microbiology 26 (1999) 259-265; Schuetz P. et al. Diabetes Care 2011, Vol. 34, 771-778).

In a preferred embodiment of the invention the comorbidity comprising an impaired innate immune response refers to Hypertension. Subjects suffering Hypertension are characterized by having constantly activated macrophages (production of reactive oxygen species) which supports low-grade inflammatory conditions leading to endothelial damage. Secondly, the constant activation of Macrophages leads to a less vigorously response towards infectious pathogens due to the desensitization effect (Singh et al. Immunol Res. 2014 August; 59(0): 243-253; Li C. et al. Acta Biochim Biophys Sin (Shanghai). 2017 Dec. 1; 49(12):1047-1057; Rucker J. A. et al. Pflugers Arch. 2017 April; 469(3-4):419-430.).

In a preferred embodiment of the invention the comorbidity comprising an impaired innate immune response refers to Anemia. Subjects suffering Anemia are characterized by a reduced total amount of red blood cells (RBCs) in the blood which can lead to an iron deficiency. Iron is known to play a role growth-promoting and differentiation-inducing properties for immune cells. It could be shown that patients with iron deficiency anemia had a reduced phagocytic activity and oxidative burst of neutrophils (Hassan T. H. et al. Medicine (2016) 95:47).

As used herein, "diagnosis" in the context of the present invention relates to the recognition and (early) detection of a clinical condition of a subject linked to an infectious disease. Also the assessment of the severity of the infectious disease may be encompassed by the term "diagnosis".

"Prognosis" relates to the prediction of an outcome or a specific risk for a subject based on an infectious disease. This may also include an estimation of the chance of recovery or the chance of an adverse outcome for said subject.

The methods of the invention may also be used for monitoring. "Monitoring" relates to keeping track of an already diagnosed infectious disease, disorder, complication or risk, e.g. to analyze the progression of the disease or the influence of a particular treatment or therapy on the disease progression of the disease of a critically ill patient or an infectious disease in a patient.

The term "therapy monitoring" or "therapy control" in the context of the present invention refers to the monitoring and/or adjustment of a therapeutic treatment of said subject, for example by obtaining feedback on the efficacy of the therapy.

In the present invention, the terms "risk assessment" and "risk stratification" and "therapy stratification" relate to the grouping of subjects into different risk groups according to their further prognosis. Risk assessment also relates to stratification for applying preventive and/or therapeutic measures. The term "therapy stratification" in particular relates to grouping or classifying patients into different groups, such as risk groups or therapy groups that receive certain differential therapeutic measures depending on their classification. The term "therapy stratification" also relates to grouping or classifying patients with infections or having symptoms of an infectious disease into a group that are not in need to receive certain therapeutic measures.

As used herein, the term "therapy guidance" refers to application of certain therapies or medical interventions based on the value of one or more biomarkers and/or clinical parameter and/or clinical scores.

It is understood that in the context of the present invention "determining the level of procalcitonin or fragment(s) thereof" or the like refers to determining procalcitonin or a fragment thereof. The fragment can have any length, e.g. at least about 5, 10, 20, 30, 40, 50 or 100 amino acids, so long as the fragment allows the unambiguous determination of the level of the procalcitonin.

As used herein, "procalcitonin" or "PCT" relates to a peptide spanning amino acid residues 1-116, 2-116, 3-116, or fragments thereof, of the procalcitonin peptide. PCT is a peptide precursor of the hormone calcitonin. Thus the length of procalcitonin fragments is at least 12 amino acids, preferably more than 50 amino acids, more preferably more than 110 amino acids. PCT may comprise post-translational modifications such as glycosylation, liposidation or derivatisation. Procalcitonin is a precursor of calcitonin and katacalcin. Thus, under normal conditions the PCT levels in the circulation are very low (<about 0.05 ng/ml).

The level of PCT in the sample of the subject can be determined by immunoassays as described herein. As used herein, the level of ribonucleic acid or deoxyribonucleic acids encoding "procalcitonin" or "PCT" can also be determined. Methods for the determination of PCT are known to a skilled person, for example by using products obtained from Thermo Fisher Scientific/B•R•A•H•M•S GmbH.

The determination of procalcitonin and fragments thereof also encompass measuring and/or detecting specific subregions of these molecules, for example by employing antibodies or other affinity reagents directed against a particular portion of the molecules, or by determining the presence and/or quantity of the molecules by measuring a portion of the protein using mass spectrometry.

The methods and kits of the present invention can also comprise determining at least one further biomarker, marker, clinical score and/or parameter in addition to PCT.

As used herein, a parameter is a characteristic, feature, or measurable factor that can help in defining a particular system. A parameter is an important element for health- and physiology-related assessments, such as a disease/disorder/clinical condition risk, preferably organ dysfunction(s). Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation II (APACHE II), the simplified acute physiology score (SAPS II score), quick sequential organ failure assessment score (qSOFA), sequential organ failure assessment score (SOFA score), body mass index, weight, age, sex, IGS II, liquid intake, white blood cell count, sodium, potassium, temperature, blood pressure, dopamine, bilirubin, respiratory rate, partial pressure of oxygen, World Federation of Neurosurgical Societies (WFNS) grading, and Glasgow Coma Scale (GCS).

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker or biomarker is defined as a characteristic that can be objectively measured and evaluated as an indicator of normal biological processes, pathogenic processes, or pharmacologic responses to a therapeutic intervention. Biomarkers may be measured in a sample (as a blood, plasma, urine, or tissue test).

The at least one further marker and/or parameter of said subject can be selected from the group consisting of a level of lactate in said sample, a level of proAdrenomedullin or fragments thereof in said sample, the sequential organ failure assessment score (SOFA score) of said subject, the simplified acute physiology score (SAPSII) of said subject, the Acute Physiology and Chronic Health Evaluation II (APACHE II) score of said subject and a level of the soluble fms-like tyrosine kinase-1 (sFlt-1), Histone H2A, Histone H2B, Histone H3, Histone H4, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24), Interleukin-22 (IL-22), Interleukin (IL-20) other ILs, Presepsin (sCD14-ST), Lipopolysaccharide Binding Protein (LBP), Alpha-1-Antitrypsin, Matrix Metalloproteinase 2 (MMP2), Metalloproteinase 2 (MMP8), Matrix Metalloproteinase 9 (MMP9), Matrix Metalloproteinase 7 (MMP7, Placental growth factor (PlGF), Chromogranin A, S100A protein, S100B protein and Tumor Necrosis Factor α (TNFα), Neopterin, pro-arginine vasopressin (AVP, proAVP or Copeptin), atrial natriuretic peptide (ANP, pro-ANP), Endothelin-1, E-selectin, ICAM-1, sICAM-1, VCAM-1, IP-10, CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, FAM19A5, CLCF1, CNTF, IL11, IL31, IL6, Leptin, LIF, OSM, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, BAFF, 4-1BBL, TNFSF8, CD40LG, CD70, CD95L/CD178, EDA-A1, TNFSF14, LTA/TNFB, LTB, TNFa, TNFSF10, TNFSF11, TNFSF12, TNFSF13, TNFSF15, TNFSF4, IL18, IL18BP, IL1A, IL1B, IL1F10, IL1F3/IL1RA, IL1F5, IL1F6, IL1F7, IL1F8, IL1RL2, IL1F9, IL33 or a fragment thereof.

Lactate, or lactic acid, is an organic compound with the formula $CH_3CH(OH)COOH$, which occurs in bodily fluids including blood. Blood tests for lactate are performed to determine the status of the acid base homeostasis in the body. Lactic acid is a product of cell metabolism that can accumulate when cells lack sufficient oxygen (hypoxia) and must turn to a less efficient means of energy production, or when a condition causes excess production or impaired clearance of lactate. Lactic acidosis can be caused by an inadequate amount of oxygen in cells and tissues (hypoxia), for example if someone has a condition that may lead to a decreased amount of oxygen delivered to cells and tissues, such as shock, septic shock or congestive heart failure, the lactate test can be used to help detect and evaluate the severity of hypoxia and lactic acidosis.

C-reactive protein (CRP) is a pentameric protein, which can be found in bodily fluids such as blood plasma. CRP levels can rise in response to inflammation. Measuring and charting CRP values can prove useful in determining disease progress or the effectiveness of treatments.

As used herein, the "sequential organ failure assessment score" or "SOFA score" is one score used to track a patient's status during the stay in an intensive care unit (ICU). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%.

As used herein, the quick SOFA score (qSOFA) is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die.

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) and may be determined based on 12 different physiologic parameters: AaDO2 or PaO2 (depending on FiO2), temperature (rectal), mean arterial pressure, pH arterial, heart rate, respiratory rate, sodium (serum), potassium (serum), creatinine, hematocrit, white blood cell count and Glasgow Coma Scale.

As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU. The SAPS II score can be determined at any time, preferably, at day 2. The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

As used herein, the term "sample" is a biological sample that is obtained or isolated from the patient or subject. "Sample" as used herein may, e.g., refer to a sample of bodily fluid or tissue obtained for the purpose of diagnosis, prognosis, or evaluation of a subject of interest, such as a patient. Preferably herein, the sample is a sample of a bodily fluid, such as blood, serum, plasma, cerebrospinal fluid, urine, saliva, sputum, pleural effusions, cells, a cellular extract, a tissue sample, a tissue biopsy, a stool sample and the like. Particularly, the sample is blood, blood plasma, blood serum, or urine.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4): 1250-6). The term "sepsis" used herein includes, but is not limited to, sepsis, severe sepsis, septic shock.

The term "sepsis" used herein includes, but is not limited to, sepsis, severe sepsis, and septic shock. Severe sepsis in refers to sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992).

The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia.

The term "sepsis" used herein relates to all possible stages in the development of sepsis.

The term "sepsis" also includes severe sepsis or septic shock based on the SEPSIS-2 definition (Bone et al., 2009). The term "sepsis" also includes subjects falling within the SEPSIS-3 definition (Singer et al., 2016). The term "sepsis" used herein relates to all possible stages in the development of sepsis.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

As used herein "infectious disease" comprises all diseases or disorders that are associated with bacterial and/or viral and/or fungal infections.

According to the present invention, critically ill patients, such as septic patients may need a very strict control, with respect of vital functions and/or monitoring of organ protection and may be under medical treatment.

In the context of the present invention, the term "medical treatment" or "treatment" comprises various treatments and therapeutic strategies, which comprise, without limitation, anti-inflammatory strategies, administration of ADM-antagonists such as therapeutic antibodies, si-RNA or DNA, the extracorporal blood purification or the removal of harmful substances via apheresis, dialyses, adsorbers to prevent the cytokine storm, removal of inflammatory mediators, plasma apheresis, administration of vitamins such as vitamin C, antibiotic treatment, fluid therapy, apheresis and measures for organ protection.

In a preferred embodiment, the term "medical treatment" or "treatment" comprises antibiotic treatment such as intraveneous antibiotic, oral antibiotics or topical antibiotics.

In a more preferred embodiment, the term "medical treatment" or "treatment" comprises intravenously applied antibiotic treatment.

Additionally, medical treatments of the present invention comprise, without limitation, stabilization of the blood clotting, iNOS inhibitors, anti-inflammatory agents like hydrocortisone, sedatives and analgetics as well as insulin.

"Fluid management" refers to the monitoring and controlling of the fluid status of a subject and the administration of fluids to stabilize the circulation or organ vitality, by e.g. oral, enteral or intravenous fluid administration. It comprises the stabilization of the fluid and electrolyte balance or the prevention or correction of hyper- or hypovolemia as well as the supply of blood products.

In the case of critical illness, such as sepsis or severe infections it is very important to have an early diagnosis as well a prognosis and risk assessment for the outcome of a patient to find the optimal therapy and management. The therapeutic approaches need to be very individual and vary from case to case. A therapeutic monitoring is needed for a best practice therapy and is influenced by the timing of treatment, the use of combined therapies and the optimization of drug dosing. A wrong or omitted therapy or management will increase the mortality rate hourly.

The term "comorbidity" in the context of the present invention refers to any further pathology or disease of the patient of the method of the invention that may be present in addition to a suspected infection or sepsis. Such comorbidities may comprise, without limitation, cardiovascular disease, atrial fibrillation, flutter, congestive heart failure, COPD, asthma, lung fibrosis, asbestosis, pulmonary disease, immunodeficiency, metabolic disorder (obesity), diabetes, renal disease, hypertension, stroke, transient ischemic attack (TIA), dementia, anemia, thrombosis, rheumatic disease, neuromuscular disease, malignancy or cancer.

A medical treatment of the present invention may be an antibiotic treatment, wherein one or more "antibiotics" or "antibiotic agents" may be administered if an infection has been diagnosed or symptoms of an infectious disease have been determined.

Antibiotics or antibiotic agents according to the present invention also encompass potentially the anti-fungal or anti-viral compounds used to treat a diagnosed infection or sepsis. The antibiotic agents commonly applied in the treatment of any given infection, as separated into the classes of pathogen are:

Gram positive coverage: Penicillins, (ampicillin, amoxicillin), penicillinase resistant, (Dicloxacillin, Oxacillin), Cephalosporins (1st and 2nd generation), Macrolides (Erythromycin, Clarithromycin, Azithromycin), Quinolones (gatifloxacin, moxifloxacin, levofloxacin), Vancomycin, Sulfonamide/trimethoprim, Clindamycin, Tetracyclines, Chloramphenicol, Linezolid, Synercid.

Gram negative coverage: Broad spectrum penicillins (Ticarcillin, clavulanate, piperacillin, tazobactam), Cephalosporins (2nd, 3rd, and 4th generation), Aminoglycosides, Macrolides, Azithromycin, Quinolones (Ciprofloxacin), Monobactams (Azetreonam), Sulfonamide/trimethoprim, Carbapenems (Imipenem), Chloramphenicol.

*Pseudomonas* coverage: Ciprofloxacin, Aminoglycosides, Some 3rd generation cephalosporins, 4th generation cephalosporins, Broad spectrum penicillins, Carbapenems.

Further antibiotic agents include for example Bensylpenicillin, Cefotaxim, Klaxacillin, Klindamycin, Aminoglycosides, Metronidazol, Piperacillin-Tazobactam, Meropenem, Imipinem, Erytromycin, Quinolone, Trimetoprim and Vancomycin.

Fungal treatments: Allyamines, Amphotericin B, Fluconazole and other Azoles, itraconazole, voriconazole, posaconazole, ravuconazole, echinocandins, Flucytosine, sordarins, chitin synthetase inhibitors, topoisomerase inhibitors, lipopeptides, pradimycins, Liposomal nystatin, Voriconazole, Echinocanidins, Imidazole, Triazole, Thiazole, Polyene.

Anti-viral treatments: Abacavir, Acyclovir (Aciclovir), activated caspase oligomerizer, Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Double-stranded RNA, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Morpholinos, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Ribozymes, Rifampicin, Rimantadine, Ritonavir, RNase H, protease inhibitors, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine.

Furthermore, antibiotic agents comprise bacteriophages for treatment of bacterial infections, synthetic antimicrobial peptides or iron-antagonists/iron chelator can be used. Also, therapeutic antibodies or antagonist against pathogenic structures like anti-VAP-antibodies, anti-resistant clone vaccination, administration of immune cells, such as in vitro primed or modulated T-effector cells, are antibiotic agents that represent treatment options for critically ill patients, such as sepsis patients. Further antibiotic agents/treatments or therapeutic strategies against infection or for the prevention of new infections include the use of antiseptics, decontamination products, anti-virulence agents like liposomes, sanitation, wound care, surgery.

It is also possible to combine several of the aforementioned antibiotic agents or treatments strategies.

According to the present invention PCT or fragments thereof and optionally other markers or clinical scores are employed as markers for therapy antibiotic therapy guidance, stratification and/or control in a patient suspected of having an infection.

A skilled person is capable of obtaining or developing means for the identification, measurement, determination and/or quantification of any one of the above PCT molecules, or fragments or variants thereof, as well as the other markers of the present invention according to standard molecular biological practice.

The level of PCT or fragments thereof as well as the levels of other markers of the present invention can be determined by any assay that reliably determines the concentration of the marker. Particularly, mass spectrometry (MS) and/or immunoassays can be employed as exemplified in the appended examples. As used herein, an immunoassay is a biochemical test that measures the presence or concentration of a macromolecule/polypeptide in a solution through the use of an antibody or antibody binding fragment or immunoglobulin.

Methods of determining PCT used in the context of the present invention are intended in the present invention. By way of example, a method may be employed selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analysers.

Determination of PCT or fragments thereof and optionally other markers based on antibody recognition is a preferred embodiment of the invention. As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to at least PCT or fragments thereof are used.

An antibody is considered to be specific, if its affinity towards the molecule of interest, e.g. PCT, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of PCT. Thus, the herein defined peptides can also be epitopes to which the antibodies specifically bind. Further, an antibody or an antibody binding fragment is used in the methods and kits of the invention that binds specifically to PCT or fragments thereof.

Further, an antibody or an antibody binding fragment is used in the methods and kits of the invention that binds specifically to PCT or fragments thereof and optionally to other markers of the present inventions such as PCT. Exemplary immunoassays can be luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed. Automated immunoassays are also intended, such as the KRYPTOR assay.

Alternatively, instead of antibodies, other capture molecules or molecular scaffolds that specifically and/or selectively recognize PCT or fragments thereof may be encompassed by the scope of the present invention. Herein, the term "capture molecules" or "molecular scaffolds" comprises molecules which may be used to bind target molecules or molecules of interest, i.e. analytes from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins). Affimers and the like are included.

In certain aspects of the invention, the method is an immunoassay comprising the steps of:
a) contacting the sample with
   i. a first antibody or an antigen-binding fragment or derivative thereof specific for a first epitope of said PCT or fragments thereof, and
   ii. a second antibody or an antigen-binding fragment or derivative thereof specific for a second epitope of said PCT or fragments thereof; and
b) detecting the binding of the two antibodies or antigen-binding fragments or derivates thereof to said PCT or fragments thereof.

Preferably, one of the antibodies can be labeled and the other antibody can be bound to a solid phase or can be bound selectively to a solid phase. In a particularly preferred aspect of the assay, one of the antibodies is labeled while the other is either bound to a solid phase or can be bound selectively to a solid phase. The first antibody and the second antibody can be present dispersed in a liquid reaction mixture, and wherein a first labeling component which is part of a labeling system based on fluorescence or chemiluminescence extinction or amplification is bound to the first antibody, and a second labeling component of said labeling system is bound to the second antibody so that, after binding of both antibodies to said PCT or fragments thereof to be detected, a measurable signal which permits detection of the resulting sandwich complexes in the measuring solution is generated. The labeling system can comprise a rare earth cryptate or chelate in combination with a fluorescent or chemiluminescent dye, in particular of the cyanine type.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, PCT or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733, EP0180492 or EP0539477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of PCT or fragments thereof and/or the level of any further marker of the herein provided method is determined. In particular preferred aspects, the diagnostic device is KRYPTOR®.

The level of the marker of the present invention, PCT or fragments thereof, or other markers, can also be determined by a mass spectrometric (MS) based methods. Such a method may comprise detecting the presence, amount or concentration of one or more modified or unmodified fragment peptides of the PCT in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of ADM or fragments thereof.

Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

Moreover, the levels (including reference levels) can be determined by mass spectrometric based methods, such as methods determining the relative quantification or determining the absolute quantification of the protein or fragment thereof of interest.

Relative quantification "rSRM" may be achieved by:
1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.
2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g to amount of protein analysed in each sample.
3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.
4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:
1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labelled synthetic version of the fragment peptide from the target protein that is being interrogated or the labelled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.
2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for therapy guidance, stratification and/or controlling a patient suspected of having an infection.

As used herein, "reference data" comprise reference level(s) of PCT and optionally of further markers. The levels of PCT and optionally further markers can be compared to the reference levels comprised in the reference data of the kit. The reference levels are herein described above and are exemplified also in the appended examples. The reference data can also include a reference sample to which the level of PCT and optionally further markers is compared. The reference data can also include an instruction manual how to use the kits of the invention.

The kit may additionally comprise items useful for obtaining a sample, such as a blood sample, for example the kit may comprise a container, wherein said container comprises a device for attachment of said container to a cannula or syringe, is a syringe suitable for blood isolation, exhibits an internal pressure less than atmospheric pressure, such as is suitable for drawing a pre-determined volume of sample into said container, and/or comprises additionally detergents, chaotropic salts, ribonuclease inhibitors, chelating agents, such as guanidinium isothiocyanate, guanidinium hydrochloride, sodium dodecylsulfate, polyoxyethylene sorbitan monolaurate, RNAse inhibitor proteins, and mixtures thereof, and/or A filter system containing nitro-cellulose, silica matrix, ferromagnetic spheres, a cup retrieve spill over, trehalose, fructose, lactose, mannose, poly-ethylenglycol, glycerol, EDTA, TRIS, limonene, xylene, benzoyl, phenol, mineral oil, anilin, pyrol, citrate, and mixtures thereof.

As used herein, the "detection reagent" or the like are reagents that are suitable to determine the herein described marker PCT and optionally further markers. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents, e.g. enzymes, chemicals, buffers, etc., that are used to prepare the sample for the MS analysis. A mass spectrometer can also be considered as a detection reagent. Detection reagents according to the invention can also be calibration solution(s), e.g. which can be employed to determine and compare the level of the marker(s).

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection. For any particular marker (like PCT), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Accordingly, the invention comprises the administration of an antibiotic suitable for treatment on the basis of the information obtained by the method described herein.

The present invention encompasses administration of the pharmaceutical composition of the present invention to a subject. As used herein, "administration" or "administering" shall include, without limitation, introducing the composition by oral administration. Such administering can also be performed, for example, once, a plurality of times, and/or over one or more extended periods. A single administration is preferred, but repeated administrations over time (e.g., hourly, daily, weekly, monthly, quarterly, half-yearly or yearly) may be necessary in some instances. Such administering is also preferably performed using an admixture and a pharmaceutically acceptable carrier. Pharmaceutically acceptable carriers are well known to those skilled in the art.

Administration of antibiotic treatment can relate to an intraveneous single-dose or a parenteral first-dose-loading antimicrobial therapy. Such a single first-dose-loading of an i.v. administered antibiotic treatment may occur in a hospital setting, an emergency department, a doctor's practice or another setting under supervision of medical personnel and may be followed by discharge of the patient. For example, it may be indicated in the context of the present invention that an initiation or a change in the antibiotic treatment of a patients is required, wherein that initiation or change may relate to an intraveneous single-dose or a parenteral first-dose-loading under supervision of medical personnel, which may be followed by for example oral antibiotic treatment that can occur after discharge of the patient.

Administration may also occur locally, for example by injection at the site where the antibiotic agent(s) should be active, for example by endoscopic or microinvasive means.

The composition described herein may comprise different types of carriers depending on whether it is to be administered in solid, liquid or aerosol form, and whether it need to be sterile for such routes of administration as injection. The composition of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Additionally, such compositions can comprise pharmaceutically acceptable carriers that can be aqueous or non-aqueous solutions, suspensions, and emulsions, most preferably aqueous solutions or solid formulations of various types known in the art. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The present invention is further described by reference to the following non-limiting examples.

EXAMPLES

The invention is further described by the following examples. These are not intended to limit the scope of the invention, but represent preferred embodiments of aspects of the invention provided for greater illustration of the invention described herein.

Methods of the Examples

Study Design and Setting:

This study was conducted at the emergency department at Skåne University Hospital, Malmö, Sweden. Consecutive adult patients with a clinically suspected infection were prospectively enrolled between December 2013 and February 2015. The inclusion criteria were suspected infection as judged by the attending nurse and ≥2 SIRS criteria. SIRS was defined as the following; temperature >38° C. or <36° C. or self-reported fever/chills within the past 24 hours, respiration rate >20 breaths/min and a heart rate >90 beats/min. White blood cell count (WBC count) was not used as an inclusion criteria due to the lack of measurement at arrival. The study was approved by the Regional Ethical Review Board at Lund University, Sweden (2013/635) and was conducted in accordance with the Helsinki Declaration. Informed consent was obtained from all patients or their next of kin.

Data Collection and Biomarker Measurements:

Patients were enrolled by the attending research nurse between 6 am and 6 pm, and medical records systematically reviewed for demographics, comorbidities and concomitant medications. Routine laboratory tests were performed by the certified laboratory of the Department of Clinical Chemistry at Skåne University Hospital, and microbiological tests and radiological examinations also noted. In addition, the time from emergency department presentation to the first dose of antibiotics and other treatments were registered, as was information on the requirement for supportive organ therapy such as supplemental oxygen, intravenous fluids, and the requirement for vasopressor, mechanical ventilation and renal placement therapy. Patient length of stay, admission to the ICU, 28 day and overall hospital mortality information was also registered. EDTA plasma samples were frozen within 2 hours after sample collection, stored at −80° C. and never thawed before analysis. PCT and MR-proADM were measured in all 213 samples using a commercially available double sandwich immunoassay on a KRYPTOR platform (Thermo Fisher Scientific, Germany).

Definition of Outcomes

The presence of organ dysfunction and infectious status for each patient was determined by the study physician. For patients not clearly meeting the criteria for organ dysfunction or infection, two infectious disease specialists reviewed the data and decided on the final classification. The primary outcomes were the requirement for intravenous antibiotics, time to treatment, the development of infection related organ dysfunction (severe sepsis) within a 48 hour period from enrolment, the presence of bacteremia, and all-cause 28 day mortality.

The criteria for organ dysfunction were adapted from the consensus criteria and the current SSC guidelines[23,24]. Accordingly, severe sepsis was defined as an infectious disease with at least 2 SIRS criteria, and the presence or development of hypotension, hypoperfusion and/or organ failure within 48 h after admission. Septic shock was defined as sepsis plus hypotension (systolic blood pressure <90 mmHg, or mean arterial pressure <70 mmHg) requiring fluid resuscitation or the administration of vasopressors.

Statistical Analysis:

Differences in clinical characteristics with regards to 28 day mortality were assessed using the $\chi^2$ test for categorical variables, and depending on distribution normality, either Student's t-test or the Mann-Whitney U test for continuous variables. Normally and non-normally distributed variables were expressed in terms of mean (standard deviation) and median [first quartile–third quartile], respectively. The association between antibiotic requirement, prediction of bacteremia, development of severe sepsis and prediction of mortality within 28 days with each biomarker and clinical score was assessed using area under the receiver operating characteristic curves (AUROC), logistic and Cox regression analysis. Logistic regression models were created using either biomarkers or scores in isolation, or adjusted with sex and age variables, and expressed as Odds Ratios (OR) and 95% confidence intervals [95% CI]. A two sided p<0.05 was considered statistically significant. All data were analyzed using the statistics software R (version 3.1.2).

Example 1: Patient Characteristics

A total of 213 patients were enrolled in the study, with 113 (53.1%) developing severe sepsis within the first 48 hours after presentation, and 7 (6.9%) presenting with septic shock. The average age of the total population was 67.8 years, with no significant differences between genders (50.2% male). Patients exhibited a high degree of comorbidities, which included cases of hypertension (42.2%), anemia (35.4%), coronary heart disease (22.3%), chronic obstructive pulmonary disease (18.4%) and diabetes (17.0%). An infectious origin could be established in 190 (89.2%) patients, with pulmonary (N=85; 39.9%), urinary tract (N=53; 24.9%) and soft tissue or skin (N=21; 9.9%) infections most prevalent. The overall 28 day mortality rate across the total population was 8.9%, with 203 (95.3%) patients having a SOFA score of points. All biomarkers and clinical scores were significantly higher in non-surviving patients compared to survivors. Non-survivors were also more likely to develop severe sepsis (p<0.01), have a higher number of organ failures (p<0.001), or be admitted onto the intensive care unit (p<0.05).

Patient characteristics with respect to 28 day mortality are summarised in Table 1.

Example 2: The Use of Biomarkers as an Aid in Assessing Requirement for Antibiotics Antibiotics were administered to a total of 187 (87.8%) patients within the study population. Of these patients, 164 (77.0%) were treated with intravenous antibiotics only, 6 (2.8%) were given a mix of intravenous and oral antibiotics, and 17 (8.0%) treated with oral antibiotics only. A comprehensive outline of the use of intravenous antibiotics can be found in Supplementary Table 2. The median time to initial intravenous antibiotic treatment was 93 [28-160] minutes, with 71 (43.8%) patients receiving initial antibiotic therapy within 60 minutes.

Logistic regression analysis indicated that MR-proADM had the strongest association with the requirement for intravenous antibiotics in both regression models (Table 3). Similar results were also found for PCT with the odds ratio for both markers greater than that of CRP or lactate. The addition of either PCT or MR-proADM to one another in a multivariate model significantly increased the prediction of antibiotic requirement (p<0.05).

Optimal cut-offs were subsequently calculated for all biomarkers based on AUROC analysis, resulting in PCT and MR-proADM cut-offs of 0.12 ng/mL and 1.27 nmol/L, respectively (Table 4). Subgroup analysis indicated significant differences between intravenous antibiotic requirement based on a combination of these marker cut-offs (Table 5). Interestingly, the median time to antibiotic administration in patients with MR-proADM values <1.27 nmol/L was 139 [81-209] minutes, which was significantly longer than in patients with values 1.27 nmol/L (43 [26-134] minutes; p<0.001). In contrast, there were no significant differences for PCT values.

Finally, 26 (12.6%) patients were found to have been prescribed antibiotics less than 48 hours prior to entering the ED. Whilst this had little effect on MR-proADM performance, the predictive value of PCT for antibiotic requirement was found to increase from OR [955 CI]: 4.22 [2.21-8.04] to 5.45 [2.49-11.93] when these patients were excluded from the analysis.

Example 3: Added Value of PCT and MR-proADM Combinations for Predicting the Requirement for Intravenous Antibiotics In comparison to the logistic regression analysis for individual biomarkers alone and for a multivariate model including age and gender of the patients, the addition of PCT to the MR-proADM multivariate model (age+gender) (Table 6) and that addition of MR-proADM to the PCT multivariate model (age+gender) (Table 7) showed that MR-proADM adds more value to PCT for predicting the requirement for intravenous antibiotics (as evidenced by the higher added $LR^2$ number, and the lower p-value for significance) than PCT does to MR-proADM. However, both combinations were significant.

Similarities can also be found when patients who were previously on antibiotic treatment (and therefore artificially decreasing the PCT concentration on arrival to the ED) were excluded from the analysis as shown in Table 8 for individual markers alone and in Table 9 for the multivariate model including age and gender. Addition of PCT to the MR-proADM multivariate model (age+gender) (Table 10) and addition of MR-proADM to the PCT multivariate model (age+gender) (Table 11) showed that both combinations were significant.

Example 4: Prediction of Bacteraemia and Development of Severe Sepsis

A positive blood culture could be obtained in 34 (16.1%) patients, with *Escherichia coli* (n=9), *Staphylococcus aureus* (n=4) and *Klebsiella pneumonia* (n=4) the most prevalent pathogens. The use of PCT had the strongest predictive value for bacteraemia (OR [95% CI]: 3.73 [2.14-6.51]), although within a multivariate model, the greatest predictive value could be found with MR-proADM (OR [95% CI]: 4.24 [2.31-7.76]); Table 12). Interestingly, the addition of MR-proADM to the multivariate model containing PCT could significantly increase predictive value (p<0.05), whereas PCT did not add to the corresponding model containing MR-proADM. Additional AUROC analysis is reported in Table 13.

Similar results could also be found for the development of severe sepsis within 48 hours of ED admission, with MR-proADM having the greatest predictive value (OR [95% CI]: 5.79 [3.30-10.16]) followed by PCT (OR [95% CI]: 4.33 [2.58-7.27]; Table 14 and Table 15). The use of lactate and CRP were relatively poor predictors of severe sepsis development (OR [95% CI]: 2.31 [1.48-3.61] and 1.94 [1.28-2.95], respectively).

Example 5: Prediction of all Cause 28 Day Mortality

AUROC and Cox regression analysis indicated that MR-proADM had the greatest performance in assessing disease severity, when measured in terms of overall 28 day mortality. Whilst there were no significant differences between the performance of MR-proADM and SOFA, values were consistently higher for MR-proADM in AUROC (AUROC [95% CI]: 0.86 [0.79-0.92] vs. 0.84 [0.77-0.91]; Table 16), univariate Cox regression (Hazard Ratio [95% CI]: 4.29 [2.54-7.26] vs. 3.29 [2.13-5.08]) and multivariate Cox regression (Hazard Ratio [95% CI]: 3.73 [2.12-5.58] vs. 2.77 [1.76-4.37]) analysis (Table 17).

In addition, AUROC analysis indicated an optimal sensitivity and specificity cut-off for MR-proADM of 1.73 nmol/L. When this cut-off was applied to the total patient population, 143 (67.1%) patients were found to have values of <1.73 nmol/L, with a resulting 28 day mortality rate of 1.4%, whereas 70 (32.9%) patients had values 1.73 nmol/L, with a corresponding 28 mortality rate of 24.3% (Hazard Ratio [95% CI] above cut-off vs. below cut-off: 15.0 [3.2-68.0]).

Finally, it could be observed that qSOFA had extremely high hazard ratios (HR IQR [95% CI]: 30.12 [5.56-163.24]; Table 16) in predicting 28 day mortality, however sensitivity at a cut-off of 2 points was relatively low (0.58 [0.36-0.77]). Indeed, of the 19 patients within this study that died within 28 days, 8 patients (42.1%) had a qSOFA score of <2 points. In each case, MR-proADM values were greater than 1.73 nmol/L.

Discussion of Examples

This study, for the first time, introduces the use of MR-proADM as a marker of sepsis disease severity in the emergency department, and uniquely highlights the importance of an early and accurate assessment of disease severity in terms of subsequent treatment decisions and likelihood of disease progression.

Such an assessment is essential in providing the appropriate level of treatment at the earliest opportunity. Indeed, it has been shown that for every hour of delay in administrating antibiotics, mortality can increase by almost 8% in the most severe cases[25]. However, relatively stable clinical signs and symptoms, in combination with low levels of diagnostic biomarkers, such as PCT and CRP, may lead to a delay in treatment whilst the severity of the patient's infectious condition is assessed. In these circumstances, biomarkers which are significantly increased earlier in the pathophysiological process may offer a rapid tool for assessing the need of immediate intravenous antibiotic treatment, and the requirement for specific sepsis therapies.

Accordingly, this study found that the use of mid-regional proadrenomedullin may fulfil this clinical requirement. Previous investigations have shown adrenomedullin to be increased in response to vascular permeability, endothelial and microcirculatory damage[14, 17, 18, 26, 27], all of which are likely to precede any subsequent complications in organ function[28, 29].

Our results show that MR-proADM performance at the earliest point of clinical contact is greater than that of all conventional biomarkers in assessing disease severity. Similar results were found in a previous intensive care sepsis study[30], which grouped patients according to existing organ dysfunction, and found superior MR-proADM performance in the low (SOFA 6) and intermediate (SOFA between 8-13 points) severity groups. The low organ severity group is of particular interest, because not only does it "represent the earliest presentation in the clinical course of sepsis and/or the less severe form of the disease"[30], but it also represents the largest infectious population entering clinical care. Furthermore, the similarities in cut-offs between the two study populations (1.73 vs. 1.79 nmol/L), as well as the high sensitivity values for predicting 28 day mortality (89% vs. 83%) strengthen the potential use of this biomarker in an ED setting, where the early stages of the disease are more prevalent. In addition, the use of a cut-off of 1.73 nmol/L found within this study can help identify a high risk infectious patient population, where potential therapies should be applied without delay.

Similarities with a previous study could also be found in the issues surrounding the use of qSOFA[11]. In both studies, extremely low sensitivities for predicting infectious related mortalities could be found (58% and 52%), with a significant proportion of non-surviving patients initially having a qSOFA score of 0 or 1 point. Interestingly, in each of these patients, MR-proADM values were 1.73 nmol/L, thus highlighting the use of the marker as an early tool for disease severity assessment—in this case being significantly increased earlier than established clinical signs and symptoms.

Whilst a limited number of studies using MR-proADM have focussed on overall mortality in patients presenting to the emergency department[19-21], the use of MR-proADM concerning antibiotic administration and time to antibiotic treatment in sepsis patients has not been previously investigated. Whilst PCT is generally considered the optimal biomarker for antibiotic guidance in the ICU[31-33], many studies have found conflicting results as to its use in the emergency department[34,36]. Our results show that PCT was found to be a more accurate biomarker of antibiotic requirement and bacteraemia than CRP or lactate, however the use of MR-proADM was superior in comparison to all conventionally used biomarkers. Reasons for this may be, in part, due to the rapidly induced kinetics of the biomarker, which is increased significantly earlier than either PCT or CRP in response to lipopolysaccharide (LPS) stimulation[36-38]. This was also confirmed in a separate study investigating sepsis development in burns patients, with MR-proADM concentrations significantly increased one day before the diagnosis of sepsis, whereas PCT levels were significantly increased on the day of infection[39].

For this study, detailed information on antibiotic administration, time to treatment, and disease progression were noted for each patient, as well as comparisons between the current gold standards of disease severity identification and the novel biomarker, MR-proADM. All patients were thoroughly reviewed by disease specialists to ensure correct diagnoses.

In conclusion, MR-proADM may offer a rapid diagnostic alternative to complex clinical scores in assessing disease severity, and can provide useful clinical information concerning the immediate requirement of antibiotics, the likelihood of disease progression, and the requirement for alternative treatment strategies in order to prevent an unfavourable outcome.

Tables

TABLE 1

Patient characteristics with regards to 28 day mortality

| | Total (n = 213) | Survivors (n = 194) | Non-Survivors (n = 19) | p-value* |
|---|---|---|---|---|
| Age | 67.8 (19.2) | 66.4 (19.2) | 82.2 (11.1) | <0.0001 |
| Male gender | 107 (50.2%) | 95 (88.8%) | 12 (11.2%) | 0.3367 |
| Diagnosis Group | | | | |
| Sepsis | 100 (46.9%) | 96 (96.0%) | 4 (4.0%) | 0.0116 |
| Severe sepsis | 113 (53.6%) | 98 (50.5%) | 15 (78.9%) | 0.0040 |
| ICU admission | 7 (3.3%) | 4 (2.1%) | 3 (15.8%) | 0.0171 |
| Comorbidities | | | | |
| Cardiovascular disease | 47 (22.3%) | 41 (91.1%) | 6 (8.9%) | 0.3838 |
| Atrial fibrillation flutter | 54 (25.6%) | 44 (22.9%) | 10 (52.6%) | 0.0103 |
| Congestive Heart Failure | 33 (15.6%) | 25 (13.0%) | 8 (42.1%) | 0.0034 |
| COPD | 39 (18.4%) | 32 (16.6%) | 7 (36.8%) | 0.0552 |
| Asthma | 14 (6.6%) | 12 (6.2%) | 2 (10.5%) | 0.3610 |
| Fibrosis/Asbestos | 4 (1.9%) | 4 (2.1%) | 0 (0.0%) | 1.0000 |
| Other Pulmonary Disease | 3 (1.4%) | 3 (1.6%) | 0 (0.0%) | 1.0000 |
| Immunodeficiency | 15 (7.1%) | 14 (7.3%) | 1 (5.6%) | 1.0000 |

TABLE 1-continued

Patient characteristics with regards to 28 day mortality

|  | Total (n = 213) | Survivors (n = 194) | Non-Survivors (n = 19) | p-value* |
|---|---|---|---|---|
| Diabetes | 36 (17.0%) | 31 (16.1%) | 5 (26.3%) | 0.3316 |
| Renal disease | 16 (7.6%) | 14 (7.3%) | 2 (10.5%) | 0.6433 |
| Hypertension | 89 (42.2%) | 77 (39.9%) | 12 (66.7%) | 0.0435 |
| Stroke/TIA | 34 (16.2%) | 30 (15.6%) | 4 (22.2%) | 0.5020 |
| Dementia | 5 (2.4%) | 5 (2.6%) | 0 (0.0%) | 1.0000 |
| Anemia | 74 (35.4%) | 64 (33.3%) | 10 (58.8%) | 0.0606 |
| Thrombosis | 24 (11.5%) | 21 (11.0%) | 3 (16.7%) | 0.4421 |
| Rheumatic Disease | 14 (6.6%) | 13 (6.8%) | 1 (5.3%) | 1.0000 |
| Neuromuscular Disease | 6 (2.8%) | 6 (3.1%) | 0 (0.0%) | 1.0000 |
| Malignancy | 53 (25.1%) | 46 (23.8%) | 7 (38.9%) | 0.1645 |
| Organ dysfunction | | | | |
| Number of organ dysfunctions | 1 [0-2] | 1 [0-1.25] | 3 [1-3] | <0.0001 |
| Neurological | 32 (15.0%) | 23 (11.9%) | 9 (47.4%) | 0.0004 |
| Cardiovascular | 45 (21.1%) | 36 (18.6%) | 9 (47.4%) | 0.0068 |
| Respiratory | 69 (32.4%) | 56 (28.9%) | 13 (68.4%) | 0.0012 |
| Renal | 26 (12.2%) | 21 (10.8%) | 5 (26.3%) | 0.0635 |
| Hepatic | 3 (1.4%) | 3 (1.6%) | 0 (0.0%) | 1.0000 |
| Haematological | 10 (4.7%) | 7 (3.6%) | 3 (15.8%) | 0.0485 |
| Metabolic acidosis | 25 (11.7%) | 19 (9.8%) | 6 (31.6%) | 0.0135 |
| Origin of infection | | | | |
| Positive blood culture | 34 (16.0%) | 30 (15.5%) | 4 (23.5%) | 0.4873 |
| Pulmonary | 71 (33.3%) | 65 (33.5%) | 6 (31.6%) | 1.0000 |
| Upper airway | 14 (6.6%) | 14 (7.2%) | 0 (0.0%) | 0.6197 |
| Urinary tract | 53 (24.9%) | 51 (26.3%) | 2 (10.5%) | 0.1688 |
| Skeletal/Joint | 1 (0.5%) | 1 (0.5%) | 0 (0.0%) | 1.0000 |
| Skin/Soft tissue | 21 (9.9%) | 16 (8.3%) | 5 (26.3%) | 0.0265 |
| CNS | 1 (0.5%) | 1 (0.5%) | 0 (0.0%) | 1.0000 |
| Abdomen | 12 (5.6%) | 11 (5.7%) | 1 (5.3%) | 1.0000 |
| Foreign object | 2 (0.9%) | 1 (0.5%) | 1 (5.3%) | 0.1708 |
| Unknown | 2 (0.9%) | 2 (1.0%) | 0 (0.0%) | 1.0000 |
| Other | 13 (6.1%) | 13 (6.7%) | 0 (0.0%) | 0.6120 |
| Treatment | | | | |
| Corticosteroids | 18 (8.5%) | 15 (7.8%) | 3 (15.8%) | 0.2091 |
| Mechanical ventilation | 2 (0.9%) | 1 (0.5%) | 1 (5.3%) | 0.0265 |
| Non-invasive ventilation | 5 (2.5%) | 2 (1.1%) | 3 (16.7%) | 0.0010 |
| Renal replacement | 2 (1.0%) | 2 (1.1%) | 0 (0.0%) | 1.0000 |
| CPAP | 1 (0.5%) | 1 (0.5%) | 0 (0.0%) | 1.0000 |
| Biomarker and clinical severity score values | | | | |
| MR-proADM | 1.36 [0.93-2.21] | 1.30 [0.89-1.82] | 2.65 [1.91-4.70] | <0.0001 |
| PCT | 0.25 [0.10-1.40] | 0.22 [0.09-1.09] | 0.98 [0.21 -6.41] | 0.0032 |
| CRP | 76 [25-163] | 71 [24-152.51] | 134 [72.5-232] | 0.0230 |
| Lactate | 1.7 [1.2-2.7] | 1.7 [1.2-2.6] | 2.4 [1.3-3.5] | 0.0453 |
| SOFA | 2 [1-4] | 2 [1-4] | 5 [3-6] | <0.0001 |
| qSOFA | 1 [1-1] | 1 [1-1] | 2 [1-2] | 0.0007 |

Apart from age (medium and standard deviation), continuous data are given as median (interquartile range).
Dichotomous variables are given as counts (%).
*Refers to difference between 28-day survivors and non-survivors.

TABLE 2

Use of intravenous antibiotics during ED treatment

| Antibiotic type | No. of patients administered (N) | Time to treatment | 28 day mortality rate (N, %) |
|---|---|---|---|
| No intravenous antibiotics | 43 (20.2%) | n/a | 2 (4.7%) |
| Single i.v. antibiotic use | 131 (79.9%) | 137.9 mins | 12 (8.6%) |
| Bensylpenicillin | 36 | 148.1 | |
| Cefotaxim | 76 | 138.9 | |
| Klaxacillin | 4 | 112.3 | |
| Klindamycin | 0 | n/a | |
| Aminoglycosides | 0 | n/a | |
| Metronidazol | 0 | n/a | |
| Piperacillin-Tazobactam | 8 | 101.8 | |
| Meropenem | 4 | 122.8 | |
| Imipinem | 1 | n/a | |
| Erytromycin | 0 | n/a | |
| Quinolone | 0 | n/a | |
| Trimetoprim | 1 | n/a | |
| Vancomycin | 0 | n/a | |
| Others | 1 | n/a | |
| Dual i.v. antibiotic use | 27 (16.5%) | 70.5 | 5 (18.5%) |
| Cefotaxim-Aminoglycosides | 10 | 65.4 | |
| Cefotaxim-Metronidazol | 2 | n/a | |
| Cefotaxim-Erytromycin | 4 | 95.1 | |
| Klinamycin- | 3 | n/a | |

TABLE 2-continued

Use of intravenous antibiotics during ED treatment

| Antibiotic type | No. of patients administered (N) | Time to treatment | 28 day mortality rate (N, %) |
|---|---|---|---|
| Aminoglycosides Klinamycin-Bensylpenicillin | 1 | n/a | |
| Klinamycin-Meropenem | 1 | n/a | |
| Aminoglycosides-Piperacillin/Tazobactam | 3 | n/a | |
| Piperacillin/Tazobactam-Meropenem | 1 | n/a | |
| Iminipenem-Vancomycin | 1 | n/a | |
| Aminoglycosides-Bensylpenicillin | 1 | n/a | |
| Triple i.v. antibiotic use | 3 (1.8%) | n/a | 0 (0.0%) |
| Bensylpenicillin-Cefotaxim-Quinolone | 1 | n/a | |
| Cefotaxim-Aminoglycosides-Piperacillin/Tazobactam | 1 | n/a | |
| Metronidazol-Quinoline-Ciprofloxacin | 1 | n/a | |

TABLE 3

Logistic regression analysis for the requirement of intravenous antibiotics upon ED presentation

| | N | Events | LR c$^2$ | DF | p value | C Index | OR [95% CI] |
|---|---|---|---|---|---|---|---|
| MR-proADM | 213 | 164 | 31.72 | 1 | 0.0000 | 0.755 | 4.34 [2.40-7.87] |
| PCT | 213 | 164 | 25.62 | 1 | 0.0000 | 0.744 | 4.22 [2.21-8.04] |
| Lactate | 204 | 158 | 10.63 | 1 | 0.0011 | 0.660 | 2.37 [1.37-4.11] |
| CRP | 207 | 159 | 13.97 | 1 | 0.0002 | 0.683 | 2.30 [1.47-3.62] |
| MR-proADM + Age + Gender | 213 | 164 | 32.79 | 3 | 0.0000 | 0.755 | 5.09 [2.44-10.63] |
| PCT + Age + Gender | 213 | 164 | 28.76 | 3 | 0.0000 | 0.756 | 3.81 [2.00-7.27] |
| Lactate + Age + Gender | 204 | 158 | 14.74 | 3 | 0.0020 | 0.686 | 2.00 [1.13-3.54] |
| CRP + Age + Gender | 207 | 159 | 19.88 | 3 | 0.0002 | 0.723 | 2.24 [1.41-3.56] |

TABLE 4

AUROC analysis for the requirement of intravenous antibiotics

| | AUROC Cut-off | Sensitivity | Specificity | PPV | NPV | LR+ | LR− |
|---|---|---|---|---|---|---|---|
| MR-proADM | 1.27 | 0.66 [0.58-0.73] | 0.80 [0.66-0.89] | 0.92 [0.85-0.95] | 0.41 [0.32-0.51] | 3.23 [1.84-5.67] | 0.43 [0.33-0.55] |
| PCT | 0.12 | 0.80 [0.74-0.86] | 0.63 [0.49-0.75] | 0.88 [0.82-0.92] | 0.49 [0.37-0.61] | 2.19 [1.51-3.19] | 0.31 [0.21-0.45] |
| Lactate | 2.1 | 0.44 [0.36-0.51] | 0.85 [0.72-0.92] | 0.91 [0.82-0.95] | 0.30 [0.23-0.39] | 2.87 [1.42-5.81] | 0.66 [0.55-0.80] |
| CRP | 40 | 0.66 [0.58-0.73] | 0.69 [0.55-0.80] | 0.88 [0.80-0.92] | 0.38 [0.28-0.48] | 2.11 [1.37-3.26] | 0.49 [0.37-0.66] |

TABLE 5

Subgroup analysis for antibiotic treatment based on PCT and MR-proADM cut-offs

| Patient Group | PCT concentration (ng/ml) | MR-proADM Concentration (nmol/L) | Patients (N) | Mortality (N, %) | Intravenous antibiotic requirement (N, %) | OR [95% CI] |
|---|---|---|---|---|---|---|
| 1 | <0.12 | <1.27 | 46 | 0 (0.0%) | 19 (41.3%) | 0.12 [0.09-0.51]* |
| 2 | <0.12 | ≥1.27 | 18 | 2 (11.1%) | 14 (77.8%) | n.s.** |
| 3 | ≥0.12 | <1.27 | 48 | 0 (0.0%) | 37 (77.1%) | 0.20 [0.06-0.71]*** |
| 4 | ≥0.12 | ≥1.27 | 101 | 17 (16.8%) | 94 (93.1%) | 0.05 [0.02-0.13]**** |

Subgroup analysis:
*Group 1 vs. Group 2;
**Group 2 vs. Group 3;
***Group 1 vs. Group 3;
****Group 1 vs. Group 4.
PCT: Procalcitonin;
MR-proADM; Mid-regional proadrenomedullin;
N: Number;
OR: Odds ratio;
CI: Confidence Interval

TABLE 6

Addition of PCT to the MR-proADM multivariate model (age + gender)

| | N | Events | LR $c^2$ | DF | p-value | C-index | Added $LR^2$ | p-value for new model |
|---|---|---|---|---|---|---|---|---|
| PCT + MR-proADM | 213 | 164 | 37.70778 | 4 | 1.29E−07 | 0.767795 | 4.92 | 0.026 |

TABLE 7

Addition of MR-proADM to the PCT multivariate model (age + gender)

| | N | Events | LR $c^2$ | DF | p-value | C-index | Added $LR^2$ | p-value for new model |
|---|---|---|---|---|---|---|---|---|
| MR-proADM + PCT | 213 | 164 | 37.71 | 4 | 1.29E−07 | 0.767795 | 8.9492 | 0.002776 |

TABLE 8

Individual biomarkers alone

| | N | Events | LR $c^2$ | DF | p-value | C-index | OR [95% CI] |
|---|---|---|---|---|---|---|---|
| MR-proADM | 187 | 147 | 27.71489 | 1 | 1.41E−07 | 0.761139 | 4.44 [2.32-8.49] |
| PCT | 187 | 147 | 24.8166 | 1 | 6.31E−07 | 0.751276 | 4.90 [2.35-10.23] |
| Lactate | 179 | 141 | 9.454986 | 1 | 0.002106 | 0.666013 | 2.42 [1.33-4.40] |
| CRP | 181 | 142 | 8.233092 | 1 | 0.004113 | 0.656013 | 2.00 [1.24-3.23] |

TABLE 9

Multivariate model including age and gender

| | N | Events | LR $c^2$ | DF | p-value | C-index | OR [95% CI] |
|---|---|---|---|---|---|---|---|
| MR-proADM + Age + Gender | 187 | 147 | 27.88646 | 3 | 3.84E−06 | 0.759524 | 4.84 [2.20-10.65] |
| PCT + Age + Gender | 187 | 147 | 28.32618 | 3 | 3.1E−06 | 0.771173 | 4.44 [2.13-9.28] |
| Lactate + Age + Gender | 179 | 141 | 13.35143 | 3 | 0.003935 | 0.699048 | 2.04 [1.10-3.78] |
| CRP + Age + Gender | 181 | 142 | 14.22562 | 3 | 0.002614 | 0.713254 | 1.92 [1.17-3.14] |

TABLE 10

Addition of PCT to the MR-proADM multivariate model (age + gender)

| | N | Events | LR c² | DF | p-value | C-index | Added LR² | p-value for new model |
|---|---|---|---|---|---|---|---|---|
| PCT + MR-proADM | 187 | 147 | 34.14024 | 4 | 6.97E−07 | 0.776531 | 6.253776 | 0.012393 |

TABLE 11

Addition of MR-proADM to the PCT multivariate model (age + gender)

| | N | Events | LR c² | DF | p-value | C-index | Added LR² | p-value for new model |
|---|---|---|---|---|---|---|---|---|
| MR-proADM + PCT | 187 | 147 | 34.14024 | 4 | 6.97E−07 | 0.776531 | 5.814053 | 0.015899 |

TABLE 12

Logistic regression analysis for the prediction of a positive bacterial culture

| | N | Events | LR c² | DF | p value | C Index | OR [95% CI] |
|---|---|---|---|---|---|---|---|
| MR-proADM | 211 | 34 | 24.07 | 1 | 0.0000 | 0.750 | 3.41 [2.01-5.78] |
| PCT | 211 | 34 | 24.29 | 1 | 0.0000 | 0.759 | 3.73 [2.14-6.51] |
| Lactate | 202 | 34 | 16.47 | 1 | 0.0000 | 0.712 | 3.14 [1.76-5.63] |
| CRP | 206 | 33 | 2.98 | 1 | 0.0845 | 0.583 | 1.65 [0.91-3.00] |
| MR-proADM + Age + Gender | 211 | 34 | 26.86 | 3 | 0.0000 | 0.748 | 4.24 [2.31-7.76] |
| PCT + Age + Gender | 211 | 34 | 24.37 | 3 | 0.0000 | 0.759 | 3.72 [2.12-6.54] |
| Lactate + Age + Gender | 202 | 34 | 16.60 | 3 | 0.0009 | 0.712 | 3.25 [1.76-6.00] |
| CRP + Age + Gender | 206 | 33 | 3.48 | 3 | 0.3231 | 0.589 | 1.62 [0.89-2.97] |

MR-proADM; Mid-regional proadrenomedullin;
PCT: Procalcitonin;
CRP: C-reactive protein;
N: Number;
DF: Degrees of Freedom;
OR: Odds ratio;
CI: Confidence Interval

TABLE 13

AUROC analysis for the prediction of a positive blood culture

| | AUROC | Cut-off | Sensitivity | Specificity | PPV | NPV | LR+ | LR− |
|---|---|---|---|---|---|---|---|---|
| MR-proADM | 0.75 [0.66-0.84] | 1.78 | 0.65 [0.48-0.79] | 0.77 [0.70-0.82] | 0.35 [0.24-0.47] | 0.92 [0.86-0.95] | 2.79 [1.94-4.03] | 0.46 [0.29-0.73] |
| PCT | 0.76 [0.67-0.84] | 0.60 | 0.79 [0.63-0.90] | 0.69 [0.62-0.76] | 0.33 [0.24-0.44] | 0.95 [0.89-0.97] | 2.60 [1.97-3.45] | 0.30 [0.15-0.58] |
| Lactate | 0.71 [0.61-0.81] | 3 | 0.59 [0.42-0.74] | 0.88 [0.82-0.92] | 0.49 [0.34-0.64] | 0.91 [0.86-0.95] | 4.71 [2.89-7.67] | 0.47 [0.31-0.71] |
| CRP | 0.58 [0.48-0.69] | 50 | 0.79 [0.62-0.89] | 0.41 [0.34-0.48] | 0.20 [0.14-0.28] | 0.91 [0.83-0.96] | 1.34 [1.08-1.66] | 0.52 [0.26-1.02] |

TABLE 14

Logistic regression analysis for the prediction of severe sepsis development within 48 hours of ED arrival

|  | N | Events | LR $c^2$ | DF | p value | C Index | OR [95% CI] |
|---|---|---|---|---|---|---|---|
| MR-proADM | 212 | 113 | 57.07 | 1 | 0.0000 | 0.782 | 5.79 [3.30-10.16] |
| PCT | 212 | 113 | 40.82 | 1 | 0.0000 | 0.753 | 4.33 [2.58-7.27] |
| Lactate | 203 | 108 | 14.90 | 1 | 0.0001 | 0.650 | 2.31 [1.48-3.61] |
| CRP | 206 | 109 | 10.73 | 1 | 0.0011 | 0.613 | 1.94 [1.28-2.95] |
| MR-proADM + Age + Gender | 212 | 113 | 58.57 | 3 | 0.0000 | 0.790 | 4.95 [2.68-9.13] |
| PCT + Age + Gender | 212 | 113 | 60.06 | 3 | 0.0000 | 0.801 | 4.47 [2.57-7.79] |
| Lactate + Age + Gender | 203 | 108 | 29.53 | 3 | 0.0000 | 0.718 | 1.97 [1.22-3.16] |
| CRP + Age + Gender | 206 | 109 | 32.85 | 3 | 0.0000 | 0.727 | 1.97 [1.26-3.07] |

MR-proADM; Mid-regional proadrenomedullin;
PCT: Procalcitonin;
CRP: C-reactive protein;
N: Number;
DF: Degrees of Freedom;
OR: Odds ratio;
CI: Confidence Interval

TABLE 15

AUROC analysis for the prediction of severe sepsis development within 48 hours of ED arrival

|  | AUROC | Cut-off | Sensitivity | Specificity | PPV | NPV | LR+ | LR− |
|---|---|---|---|---|---|---|---|---|
| MR-proADM | 0.78 [0.72-0.84] | 1.10 | 0.86 [0.78-0.91] | 0.61 [0.51-0.70] | 0.71 [0.63-0.78] | 0.79 [0.69-0.87] | 2.18 [1.69-2.81] | 0.23 [0.14-0.38] |
| PCT | 0.75 [0.69-0.82] | 0.17 | 0.78 [0.69-0.85] | 0.62 [0.52-0.71] | 0.70 [0.61-0.77] | 0.71 [0.61-0.79] | 2.03 [1.55-2.65] | 0.36 [0.25-0.52] |
| Lactate | 0.65 [0.57-0.73] | 2.2 | 0.49 [0.40-0.58] | 0.82 [0.73-0.89] | 0.76 [0.65-0.84] | 0.59 [0.50-0.67] | 2.74 [1.71-4.40] | 0.62 [0.50-0.76] |
| CRP | 0.61 [0.63-0.76] | 48 | 0.72 [0.63-0.80] | 0.47 [0.38-0.57] | 0.61 [0.52-0.69] | 0.61 [0.49-0.71] | 1.38 [1.10-1.72] | 0.58 [0.40-0.84] |

TABLE 16

AUROC analysis for the prediction of 28 day mortality

|  | AUROC | Cut-off | Sensitivity | Specificity | PPV | NPV | LR+ | LR− |
|---|---|---|---|---|---|---|---|---|
| MR-proADM | 0.86 [0.79-0.92] | 1.73 | 0.89 [0.69-0.97] | 0.73 [0.66-0.78] | 0.24 [0.16-0.35] | 0.99 [0.95-1.00] | 3.28 [2.48-4.32] | 0.14 [0.04-0.54] |
| PCT | 0.71 [0.59-0.83] | 0.41 | 0.74 [0.51-0.88] | 0.61 [0.54-0.67] | 0.16 [0.09-0.24] | 0.96 [0.91-0.98] | 1.88 [1.36-2.59] | 0.43 [0.20-0.93] |
| Lactate | 0.64 [0.50-0.78] | 2.2 | 0.63 [0.41-0.81] | 0.69 [0.62-0.75] | 0.17 [0.10-0.28] | 0.95 [0.90-0.97] | 2.01 [1.34-3.02] | 0.54 [0.30-0.97] |
| CRP | 0.66 [0.54-0.71] | 71 | 0.83 [0.61-0.94] | 0.50 [0.43-0.57] | 0.14 [0.08-0.21] | 0.97 [0.91-0.99] | 1.66 [1.29-2.13] | 0.34 [0.12-0.95] |
| SOFA | 0.84 [0.77-0.91] | 3 | 0.95 [0.75-0.99] | 0.63 [0.56-0.69] | 0.20 [0.13-0.29] | 0.99 [0.96-1.00] | 2.55 [2.07-3.15] | 0.08 [0.01-0.57] |
| qSOFA | 0.71 [0.58-0.85] | 2 | 0.58 [0.36-0.77] | 0.81 [0.75-0.86] | 0.23 [0.14-0.37] | 0.95 [0.91-0.98] | 3.12 [1.92-5.06] | 0.52 [0.30-0.88] |

TABLE 17

AUROC and logistic regression analysis for the prediction of 28 day mortality

|  | N | Events | LR $c^2$ | DF | p value | C Index | HR IQR [95% CI] |
|---|---|---|---|---|---|---|---|
| MR-proADM | 213 | 19 | 28.11 | 1 | 0.0000 | 0.841 | 4.29 [2.54-7.26] |
| PCT | 213 | 19 | 10.05 | 1 | 0.0015 | 0.694 | 2.65 [1.46-4.82] |
| Lactate | 204 | 19 | 4.46 | 1 | 0.0346 | 0.640 | 1.99 [1.06-3.76] |
| CRP | 207 | 18 | 4.69 | 1 | 0.0303 | 0.653 | 2.37 [1.00-5.62] |
| SOFA | 213 | 19 | 22.92 | 1 | 0.0000 | 0.859 | 3.29 [2.13-5.08] |
| qSOFA | 213 | 19 | 14.63 | 1 | 0.0001 | 0.798 | 30.12 [5.56-163.24] |
| MR-proADM + Age | 213 | 19 | 35.76 | 2 | 0.0000 | 0.864 | 3.73 [2.12-6.58] |
| PCT + Age | 213 | 19 | 27.34 | 2 | 0.0000 | 0.824 | 2.87 [1.51-5.46] |
| Lactate + Age | 204 | 19 | 19.30 | 2 | 0.0001 | 0.767 | 1.70 [0.87-3.31] |
| CRP + Age | 207 | 18 | 20.25 | 2 | 0.0000 | 0.779 | 2.48 [1.01-6.09] |
| SOFA | 213 | 19 | 32.80 | 2 | 0.0000 | 0.856 | 2.77 [1.76-4.37] |
| qSOFA | 213 | 19 | 25.85 | 2 | 0.0000 | 0.811 | 15.55 [2.70-89.48] |

REFERENCES

1. Martin G S, Mannino D M, Eaton S, Moss M. The epidemiology of sepsis in the United States from 1979 through 2000. N Engl J Med. Apr. 17, 2003; 348(16):1546-1554.
2. Angus D C, Linde-Zwirble W T, Lidicker J, Clermont G, Carcillo J, Pinsky M R. Epidemiology of severe sepsis in the United States: analysis of incidence, outcome, and associated costs of care. Crit Care Med. July 2001; 29(7):1303-1310.
3. Kumar A, Roberts D, Wood K E, et al. Duration of hypotension before initiation of effective antimicrobial therapy is the critical determinant of survival in human septic shock. Crit Care Med. June 2006; 34(6):1589-1596.
4. Henriksen D P, Laursen C B, Jensen T G, Hallas J, Pedersen C, Lassen A T. Incidence rate of community-acquired sepsis among hospitalized acute medical patients—a population-based survey. Crit Care Med. January 2015; 43(1):13-21.
11. Williams J M, Greenslade J H, McKenzie J V, Chu K, Brown A F, Lipman J. Systemic Inflammatory Response Syndrome, Quick Sequential Organ Function Assessment, and Organ Dysfunction: Insights From a Prospective Database of E D Patients With Infection. Chest. March 2017; 151(3):586-596.
14. Temmesfeld-Wollbruck B, Brell B, David I, et al. Adrenomedullin reduces vascular hyperpermeability and improves survival in rat septic shock. Intensive Care Med. April 2007; 33(4):703-710.
17. Brell B, Temmesfeld-Wollbruck B, Altzschner I, et al. Adrenomedullin reduces *Staphylococcus aureus* alpha-toxin-induced rat ileum microcirculatory damage. Crit Care Med. April 2005; 33(4):819-826.
18. Vigue B, Leblanc P E, Moati F, et al. Mid-regional pro-adrenomedullin (M R-proADM), a marker of positive fluid balance in critically ill patients: results of the ENVOL study. Crit Care. Nov. 9, 2016; 20(1):363.
19. Albrich W C, Dusemund F, Ruegger K, et al. Enhancement of CURB65 score with proadrenomedullin (CURB65-A) for outcome prediction in lower respiratory tract infections: derivation of a clinical algorithm. BMC Infect Dis. 2011; 11:112.
20. Albrich W C, Ruegger K, Dusemund F, et al. Optimised patient transfer using an innovative multidisciplinary assessment in Kanton Aargau (OPTIMA I): an observational survey in lower respiratory tract infections. Swiss Med Wkly. 2011; 141:w13237.
21. Albrich W C, Ruegger K, Dusemund F, et al. Biomarker-enhanced triage in respiratory infections: a proof-of-concept feasibility trial. Eur Respir J. October 2013; 42(4):1064-1075.
23. Dellinger R P, Levy M M, Carlet J M, et al. Surviving Sepsis Campaign: international guidelines for management of severe sepsis and septic shock: 2008. Crit Care Med. January 2008; 36(1):296-327.
24. Levy M M, Fink M P, Marshall J C, et al. 2001 SCCM/ESICM/ACCP/ATS/SIS International Sepsis Definitions Conference. Crit Care Med. April 2003; 31(4):1250-1256.
25. Christ M, Grossmann F, Winter D, Bingisser R, Platz E. Modern triage in the emergency department. Dtsch Arztebl Int. December 2010; 107(50):892-898.
26. Temmesfeld-Wollbruck B, Hocke A C, Suttorp N, Hippenstiel S. Adrenomedullin and endothelial barrier function. Thromb Haemost. November 2007; 98(5):944-951.
27. Gonzalez-Rey E, Chorny A, Varela N, Robledo G, Delgado M. Urocortin and adrenomedullin prevent lethal endotoxemia by down-regulating the inflammatory response. Am J Pathol. June 2006; 168(6):1921-1930.
28. Bustamante A, Garcia-Berrocoso T, Penalba A, et al. Sepsis biomarkers reprofiling to predict stroke-associated infections. J Neuroimmunol. Nov. 15, 2017; 312:19-23.
29. Valenzuela-Sanchez F, Valenzuela-Mendez B, Rodriguez-Gutierrez J F, Estella-Garcia A, Gonzalez-Garcia M A. New role of biomarkers: mid-regional pro-adrenomedullin, the biomarker of organ failure. Ann Transl Med. September 2016; 4(17):329.
30. Andaluz-Ojeda D, Nguyen H B, Meunier-Beillard N, et al. Superior accuracy of mid-regional proadrenomedullin for mortality prediction in sepsis with varying levels of illness severity. Ann Intensive Care. December 2017; 7(1):15.
31. Bloos F, Trips E, Nierhaus A, et al. Effect of Sodium Selenite Administration and Procalcitonin-Guided Therapy on Mortality in Patients With Severe Sepsis or Septic Shock: A Randomized Clinical Trial. JAMA Intern Med. Sep. 1, 2016; 176(9):1266-1276.
32. Kopterides P, Siempos, I I, Tsangaris I, Tsantes A, Armaganidis A. Procalcitonin-guided algorithms of antibiotic therapy in the intensive care unit: a systematic review and meta-analysis of randomized controlled trials. Crit Care Med. November 2010; 38(11):2229-2241.
33. Kip M M, Kusters R, M J I J, Steuten L M. A PCT algorithm for discontinuation of antibiotic therapy is a cost-effective way to reduce antibiotic exposure in adult intensive care patients with sepsis. J Med Econ. 2015; 18(11):944-953.
34. Chan Y L, Tseng C P, Tsay P K, Chang S S, Chiu T F, Chen J C. Procalcitonin as a marker of bacterial infection in the emergency department: an observational study. Crit Care. February 2004; 8(1):R12-20.
35. Gille-Johnson P, Hansson K E, Gardlund B. Clinical and laboratory variables identifying bacterial infection and bacteraemia in the emergency department. Scand J Infect Dis. October 2012; 44(10):745-752.
36. de Kruif M D, Lemaire L C, Giebelen I A, et al. The influence of corticosteroids on the release of novel biomarkers in human endotoxemia. Intensive Care Med. March 2008; 34(3):518-522.
37. Vila G, Resl M, Stelzeneder D, et al. Plasma N T-proBNP increases in response to LPS administration in healthy men. J Appl Physiol (1985). December 2008; 105(6):1741-1745.
38. Allaker R P, Kapas S. Adrenomedullin expression by gastric epithelial cells in response to infection. Clin Diagn Lab Immunol. July 2003; 10(4):546-551.
39. Gille J, Ostermann H, Dragu A, Sablotzki A. MR-proADM: A New Biomarker for Early Diagnosis of Sepsis in Burned Patients. J Burn Care Res. September/October 2017; 38(5):290-298.
40. M. Christ-Crain: "Procalcitonin Guidance of Antibiotic Therapy Community-acquired Pneumonia: A Randomized Trial", American Journal of Respiratory and Critical Care Medicine, vol. 174, no. 1, 1 Jan. 2006, pages 84-93.
41. Philipp Schuetz et al: "Blood biomarkers for personalized treatment and patient management decisions in community-acquired pneumonia:", CURRENT OPINION ON INFECTIOUS DISEASES., vol. 26, no. 2, 1 Apr. 2013, pages 159-167.

The invention claimed is:
1. A method of treating a patient wherein the patient has one or more comorbidities wherein the method comprises
administering a pharmaceutical composition comprising one or more antibiotic agents,
wherein the patient is administered said pharmaceutical composition after being identified by the method by a method comprising:
providing a sample from said patient, and
measuring a level of PCT or fragment(s) thereof in said sample,
wherein the level of PCT or fragment(s) thereof in said sample is indicative of whether an initiation or a change of an antibiotic treatment is required
wherein the one or more comorbidities are selected from the group consisting of metabolic disorder (obesity), diabetes, immunodeficiency, renal disease, hypertension thrombosis, malignancy and cancer, and
wherein the patient is not suffering from an acute ischemic or hemorrhagic stroke.

2. Method of treating a patient according to claim 1, wherein administration of the composition is initiated within 180 minutes, preferably within 120 minutes, more preferably within 60 minutes or immediately after determining the level of PCT or fragment(s) thereof in said sample.

3. Method of treating a patient according to claim 1, wherein the patient receives intravenous administration of the composition.

4. Method of treating a patient according to claim 1, wherein the patient receives intravenous and oral administration of one or more compositions.

5. A method comprising:
treating a patient having one or more comorbidities comprising an impaired innate immune response and suspected of having an infection with an antibiotic,
wherein said patient has been determined to have, in a bodily fluid sample of the patient, a level of the PCT equal to or higher than 0.1 ng/ml.

6. The method according to claim 1, wherein the level of PCT or fragment(s) thereof in said sample is greater than the level of PCT or fragment(s) thereof in one or more control samples, indicates an escalation of antibiotic treatment, an initiation or a change of dose, a change in the route of administration and/or a change in antibiotic agent, is required.

7. The method according to claim 1, wherein the level of PCT or fragment(s) thereof in said sample indicates that a de-escalation of antibiotic treatment, or stopping antibiotic treatment, and/or a change of the setting of administration of an antibiotic treatment is required.

8. Method according to claim 1, wherein the provided sample was isolated from the patient within 12 hours from first contact with medical personnel.

9. Method according to claim 1, wherein the patient presents in an emergency department or a primary care unit.

10. Method according to claim 1, wherein a level of PCT or fragment(s) thereof in a sample equal to or above 0.05 ng/ml, preferably equal to or greater than 0.1 ng/ml, more preferably equal to or above 0.12 ng/ml, indicates that an initiation or a change of an antibiotic treatment is required.

11. Method according to claim 1, comprising additionally determining in a sample from said patient a level of at least one further biomarker, determining at least one clinical parameter and/or determining at least one clinical score.

12. Method according to claim 11, wherein the level of the at least one further biomarker is determined in the same sample as the level of PCT or fragment(s) thereof.

13. Method according to claim 1, wherein the sample for determining PCT or fragment(s) thereof is a bodily fluid, preferably selected from the group consisting of a blood sample, a serum sample, a plasma sample and/or a urine sample.

14. Method according to claim 1, wherein said patient has not yet received antibiotic treatment.

15. Method according to claim 1, wherein said patient is receiving oral antibiotic treatment and the change of an antibiotic treatment comprises a change in the route of administration of the antibiotic treatment.

* * * * *